United States Patent
Mendelsohn

(10) Patent No.: US 10,870,656 B2
(45) Date of Patent: Dec. 22, 2020

(54) METHODS FOR TREATMENT OF HEART FAILURE

(71) Applicant: Cardurion Pharmaceuticals, LLC, Cambridge, MA (US)

(72) Inventor: Michael E. Mendelsohn, Boston, MA (US)

(73) Assignee: Cardurion Pharmaceuticals, LLC, Cambridge, MA (US)

( * ) Notice: Subject to any disclaimer, the term of this patent is extended or adjusted under 35 U.S.C. 154(b) by 0 days.

(21) Appl. No.: 16/240,393

(22) Filed: Jan. 4, 2019

(65) Prior Publication Data

US 2019/0211028 A1    Jul. 11, 2019

Related U.S. Application Data

(63) Continuation of application No. PCT/US2017/041249, filed on Jul. 7, 2017.

(60) Provisional application No. 62/359,695, filed on Jul. 7, 2016.

(51) Int. Cl.
| | |
|---|---|
| *A61K 31/522* | (2006.01) |
| *C07D 495/04* | (2006.01) |
| *A61K 45/06* | (2006.01) |
| *A61K 31/519* | (2006.01) |
| *A61P 9/04* | (2006.01) |

(52) U.S. Cl.
CPC .......... *C07D 495/04* (2013.01); *A61K 31/519* (2013.01); *A61K 45/06* (2013.01); *A61P 9/04* (2018.01)

(58) Field of Classification Search
CPC .. C07D 495/04; C07D 239/00; C07D 333/00; A61K 31/522
See application file for complete search history.

(56) References Cited

U.S. PATENT DOCUMENTS

| | | | |
|---|---|---|---|
| 8,293,754 B2 | 10/2012 | Gotanda et al. | |
| 8,748,437 B2 | 6/2014 | Hayashi et al. | |
| 2008/0009498 A1 | 1/2008 | Garvey et al. | |
| 2008/0076758 A1 | 3/2008 | Folkes et al. | |
| 2009/0203703 A1 | 8/2009 | Gotanda et al. | |
| 2011/0275762 A1 | 11/2011 | Cmiljanovic et al. | |

OTHER PUBLICATIONS

Johns Hopkins Medicine, Drugs that block disease-fueling enzyme already tested for other conditions, 5 pages (2015).*
Kuhn, A big-hearted molecule, Nature, vol. 519, pp. 416-417 (Mar. 2015).*
Abdel-Megid et al. (2016) "Chemistry of Thienopyrimidines and Their Biological Applications," J. Pharm. Appl Chem. 2(3):103-127.
Blanton et al. (2012) "Protein Kinase G Iα inhibits pressure overload-induced cardiac remodeling and is required for the cardioprotective effect of sildenafil in vivo," Journal of the American Heart Association. 5(e003731):1-10.
Braunwald (2015) "The war against heart failure: the Lancet lecture," The Lancet. 385(9970):812-824.
Center for Disease Control (Jun. 16, 2016) "Heart Failure Fact Sheet," U.S. Department of Health & Human Services. 2 pages. Accessible on the Internet at URL: https://www.cdc.gov/dhdsp/data_statistics/fact_sheets/fs_heart_failure.htm.
International Search Report with Written Opinion corresponding to International Patent Application No. PCT/US2017/041249, dated Sep. 26, 2017, 8 pages.
Takimoto et al. (2005) "Chronic inhibition of cyclic GMP phosphodiesterase 5A prevents and reverses cardiac hypertrophy," Nature Medicine. 11(2):214-222.
Celanire, S., et al. "Small Molecule Therapeutics for Schizophrenia", Springer, Oct. 13, 2014, p. 292.

* cited by examiner

*Primary Examiner* — Deepak R Rao
(74) *Attorney, Agent, or Firm* — Mintz Levin Cohn Ferris Glovsky and Popeo, P.C.

(57) ABSTRACT

Disclosed are methods, compositions and kits for treating or preventing heart failure. Methods of the invention treating heart failure in a mammal comprising administering to the mammal an effective amount of a thienopyrimidine compound.

9 Claims, 12 Drawing Sheets

METHODS FOR TREATMENT OF HEART FAILURE

CROSS-REFERENCE

This application is continuation of International Application No. PCT/US2017/041249, filed Jul. 7, 2017, which in turn claims the benefit of priority to U.S. provisional application No. 62/359,695, filed Jul. 7, 2016, which is incorporated herein by reference in its entirety.

FIELD

The present invention relates to a use of one or more thienopyrimidine compounds for treating or preventing heart failure.

BACKGROUND

Heart failure is a global problem affecting 38 million patients worldwide. Heart failure is the most common diagnosis in hospitalized patients aged 65 years or older and afflicts more than six million Americans. The 5-year survival rate for heart failure is worse than most cancers and the annual cost of care for heart failure in the USA has been estimated to exceed US$30 billion (2015, Braunwald, Lancet; 385: 812-24).

In the United States, about 1 million heart failure hospital admissions occur annually. About 5.7 million adults in the United States have heart failure and about half of people who develop heart failure die within 5 years of diagnosis (heart failure fact sheet, Center for Disease Control, http://www.cdc.gov/dhdsp/data_statistics/fact_sheets/fs_heart_failure.htm).

In heart failure with reduced ejection fraction (HFrEF), also known as systolic HF, the heart muscle is not able to contract adequately and, therefore, ejects less oxygen-rich blood into the circulation. Patients with this form of the disease will have lower-than-normal left ventricular ejection fraction on an echocardiogram. Heart failure with preserved ejection fraction (HFpEF) is a second type of heart failure that lacks any therapies at present and is thus particularly problematic. HFpEF constitutes at least half of all heart failure cases. Exercise intolerance, pulmonary congestion and fatigue are notable HFpEF symptoms and result in a poor life quality.

It thus would be desirable to have new therapies for treatment of both forms of heart failure.

SUMMARY

We now provide new therapies for treatment of heart failure.

In one aspect, methods of the invention comprise administering a thienopyrimidine compound to a mammal, such as a mammal suffering from or susceptible to heart failure.

In a further aspect, methods of the invention comprise administering to a mammal an effective amount of one or more thienopyrimidine compounds, such as one or more compounds of the following Formula (I):

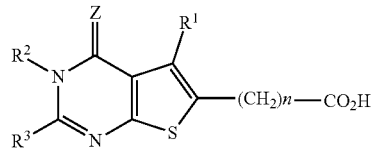

wherein:

$R^1$ is hydrogen, $C_{1-6}$ alkyl, $C_{1-6}$ alkoxy$C_{1-6}$ alkyl or $C_{1-6}$ haloalkyl containing 1-6 halogen atoms, $R^2$ is hydrogen, $C_{1-6}$ alkyl, phenyl$C_{1-6}$ alkyl or amino, $R^3$ is $C_{2-6}$ alkyl, $C_{2-6}$ alkenyl, carbamoyl$C_{1-6}$ alkyl, amino$C_{1-6}$ alkyl, $C_{1-6}$ alkylamino$C_{1-6}$ alkyl, di-($C_{1-6}$ alkyl)amino$C_{1-6}$ alkyl, $C_{1-6}$ alkylthio or Y—X group, or $R^2$ and $R^3$ may together form tetramethylene, X is a chemical bond, or $CH_2$, $CH(OH)$, $CH(C_6H_5)$, CO, $CH_2CH_2$, $CH_2CO$, $COCH_2$, S, O or NH and Y is an aromatic carbocyclic group, benzyl, aromatic heterocyclic group, 4-7-membered cycloalkyl group, 4-7-membered cycloalkenyl group, 5-7-membered saturated heterocyclic group containing 1 or 2 nitrogen atoms, or 5-7-membered saturated heterocyclic group forming a condensed ring with 5 or 6-membered saturated cyclic group and containing 1 or 2 nitrogen atoms, all of these groups optionally containing 1-3 substituents selected from halogen atom, $C_{1-6}$ alkyl, $C_{1-6}$ haloalkyl containing 1-6 halogen atoms, $C_{1-6}$ haloalkyloxy containing 1-6 halogen atoms, $C_{1-6}$ haloalkylthio containing 1-6 halogen atoms, $C_{1-6}$ alkoxy, $C_{1-6}$ alkylthio, $C_{1-4}$ alkylenedioxy, carboxyl, $C_{1-6}$ alkoxycarbonyl, oxo, amino, nitro and phenyl, Z is S or O, and n is 0 or an integer of 1-4; and pharmaceutically acceptable salts thereof.

In certain preferred aspects, Z is oxygen. In additional aspects, Z is preferably S. In certain aspects, $R^3$ comprises an aromatic group such as phenyl or benzyl, including halogen-substituted phenyl or benzyl including benzyl and phenyl substituted with fluoro or choloro. The value n is preferably 0 or 1. $R^1$ is preferably hydrogen or C1-6 alkyl such as methyl.

In particular aspects, a compound to be administered or a compound of a kit is one or more of the following compounds as set forth in the below Table A, or a pharmaceutically acceptable salt of such one or more compounds. As referred to herein, "a compound of Table A" refers to any of the compounds depicted in the immediately below Table A:

TABLE A

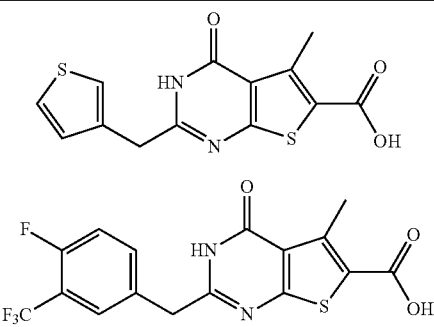

TABLE A-continued

TABLE A-continued

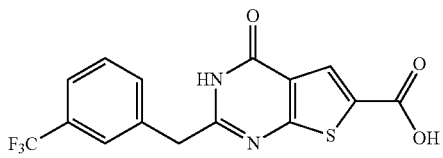
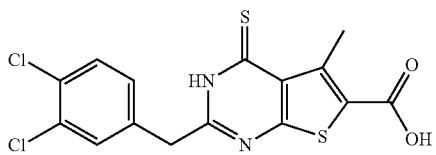
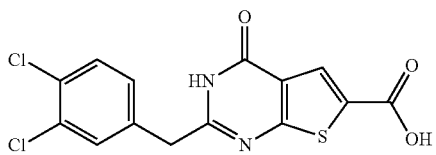
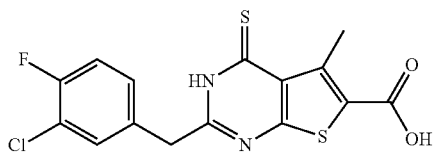
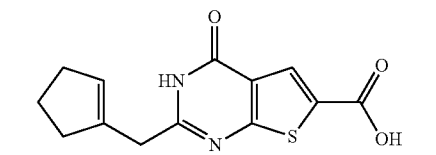
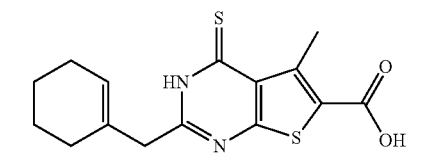 [SMILES: Cc1c(C(=O)O)sc2nc(CC3=CCCCC3)[nH]c(=S)c12]
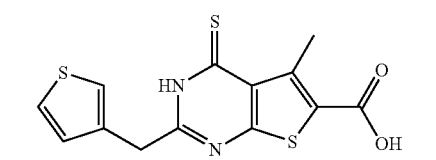
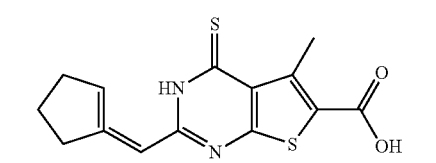
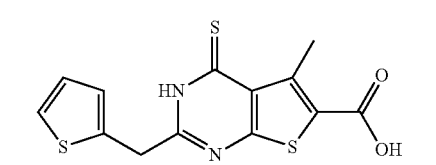 [SMILES: Cc1c(C(=O)O)sc2nc(Cc3cccs3)[nH]c(=S)c12]
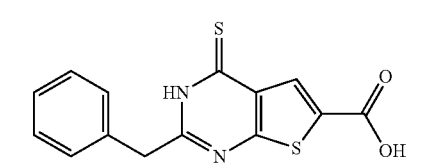 [SMILES: O=C(O)c1cc2c(=S)[nH]c(Cc3ccccc3)nc2s1]

TABLE A-continued

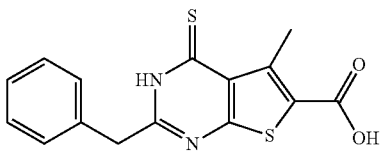 [SMILES: Cc1c(C(=O)O)sc2nc(Cc3ccccc3)[nH]c(=S)c12]
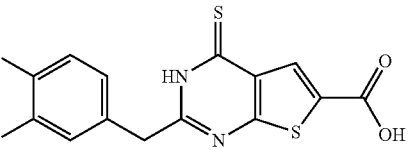
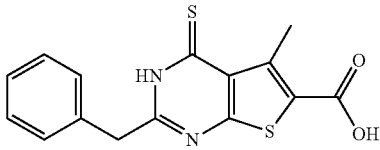 [SMILES: Cc1c(C(=O)O)sc2nc(Cc3ccccc3)[nH]c(=S)c12]
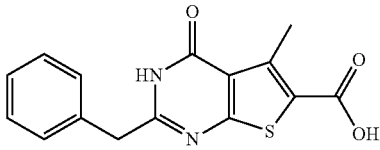 [SMILES: Cc1c(C(=O)O)sc2nc(Cc3ccccc3)[nH]c(=O)c12]

In certain additional aspects, a compound to be administered or a compound of a kit is one or more of the following compounds, or a pharmaceutically acceptable salt of one or more of the following compounds:

2-(3,4-Dichlorobenzyl)-5-methyl-4-oxo-3,4-dihydrothieno[2,3-d]pyrimidine-6-carboxylic acid;
2-(3-Chlorobenzyl)-5-methyl-4-oxo-3,4-dihydrothieno[2,3-d]pyrimidine-6-carboxylic acid;
5-Methyl-4-oxo-2-(3-trifluoromethylbenzyl)-3,4-dihydrothieno[2,3-d]pyrimidine-6-carboxylic acid;
2-(3-Chloro-4-fluorobenzyl)-5-methyl-4-oxo-3,4-dihydrothieno[2,3-d]pyrimidine-6-carboxylic acid;
2-(5-Chloro-2-fluorobenzyl)-5-methyl-4-oxo-3,4-dihydrothieno[2,3-d]pyrimidine-6-carboxylic acid;
2-(Cyclopent-1-enylmethyl)-5-methyl-4-oxo-3,4-dihydrothieno[2,3-d]pyrimidine-6-carboxylic acid;
4-Oxo-2-(thiophen-2-ylmethyl)-3,4-dihydrothieno[2,3-d]pyrimidine-6-carboxylic acid;
2-Benzyl-4-oxo-3,4-dihydrothieno[2,3-d]pyrimidine-6-carboxylic acid;
2-(3-Chlorobenzyl)-4-oxo-3,4-dihydrothieno[2,3-d]pyrimidine-6-carboxylic acid; and
4-Oxo-2-(3-trifluoromethylbenzyl)-3,4-dihydrothieno-[2,3-d]pyrimidine-6-carboxylic acid.

In additional particular aspects, a compound to be administered or a compound of a kit is one or more of the following as set forth in the Table B which follows or a pharmaceutically acceptable salt of such one or more compounds.

In additional particular aspects, a compound to be administered or a compound of a kit is one or more of the following as set forth in the Table C which follows or a pharmaceutically acceptable salt of such one or more compounds.

In certain aspects, the mammal being treated is suffering from or has suffered from heart failure. The mammal also may be suffering from or has suffered from congestive heart failure. The mammal also may be suffering from or has suffered from cardiogenic shock.

In particular embodiments, the mammal being treated is suffering from or susceptible to cardiac hypertrophy, heart failure with preserved ejection fraction (HfpEF), heart failure with reduced ejection fraction (HFrEF) (reduced systolic function), reduced diastolic function, maladaptive hypertrophy, heart failure with preserved systolic function, diastolic heart failure, hypertensive heart disease, aortic stenosis, hypertrophic cardiomyopathy, and/or post ischemic cardiac remodeling.

In a preferred aspect, a mammal that is suffering from or has suffered from heart failure is selected for heart failure treatment and a compound as disclosed herein is administered to the selected mammal. The mammal may be identified as exhibiting congestive heart failure disorder having low cardiac output and/or low stroke volume.

In preferred aspects, the treated mammal is a human.

A thienopyrimidine compound suitably can be administered in conjunction with one or more other agents distinct for treating heart failure.

Kits are also provided that suitably may comprise a thienopyrimidine compound as disclosed herein and instructions for use of the thienopyrimidine compound for treating heart failure. The instructions typically will be in written form, for example as presented on a package insert or a product label.

Use of a thienopyrimidine compound as disclosed herein can provide an increase in measured cyclic GMP levels, for example an increase of 20, 30, 40, 50, 80 or 100 percent or more measured cyclic GMP value in a subject's blood or urine sample relative to a control (blood or urine sample from the subject prior to treatment with a thienopyrimidine compound as disclosed herein.)

Other aspects of the invention are disclosed infra.

DETAILED DESCRIPTION

Figure 1A:
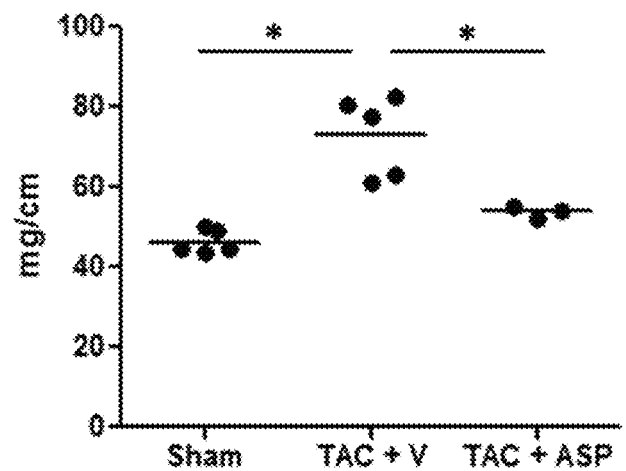
FIG. 1A shows LV masses normalized to tibia length from the mice experimental groups.
Figure 1B:
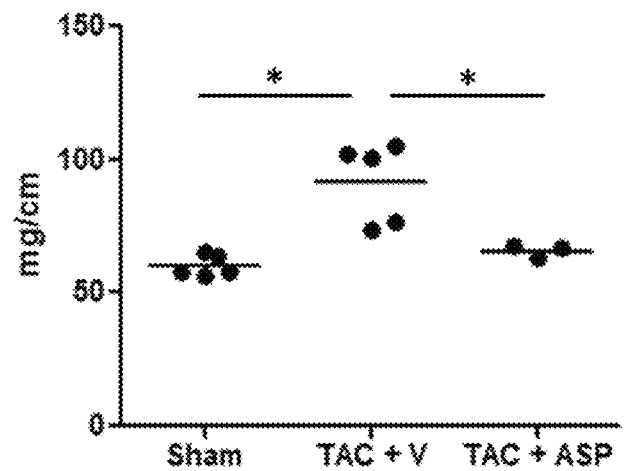
FIG. 1B shows HW masses normalized to tibia length from the mice experimental groups.
Figure 1C:
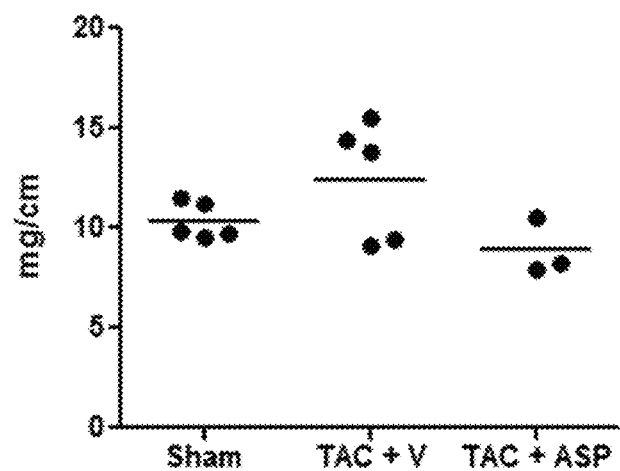
FIG. 1C shows RV masses normalized to tibia length from the mice experimental groups.
Figure 1D:
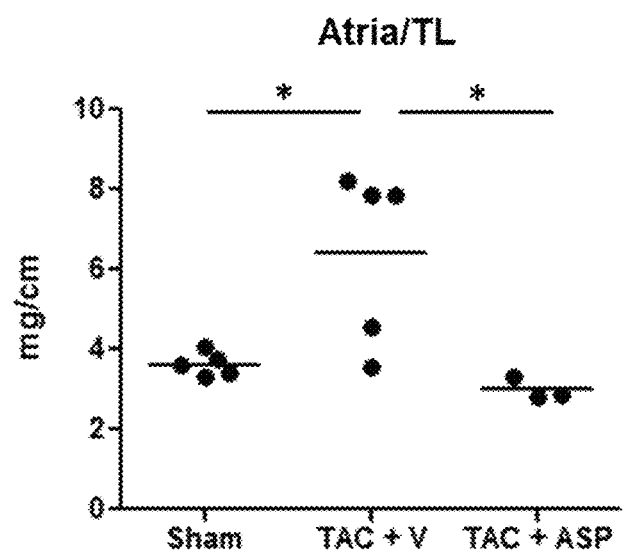
FIG. 1D shows atria masses normalized to tibia length from the mice experimental groups.
Figure 1E:
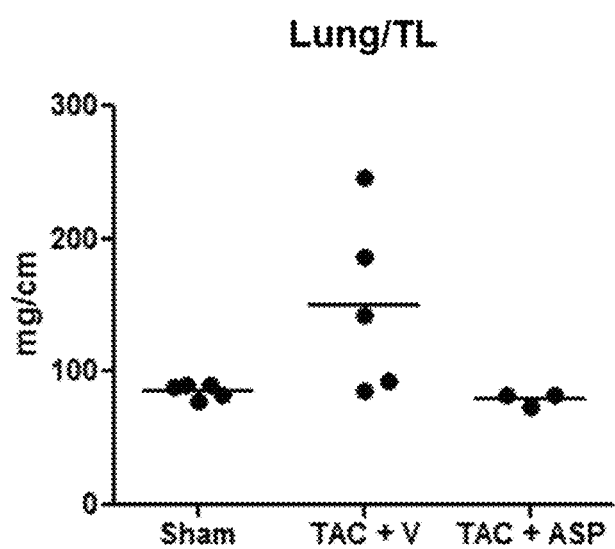
FIG. 1E shows lung masses normalized to tibia length from the mice experimental groups.

Preferred compounds of the invention may be potent inhibitors of phosphodiesterase 9 (PDE9) as determined by in vitro assay.

Preferred thienopyrimidines include optionally substituted thieno[2,3-d]pyrimidine compounds.

In the present application, the expressions, "$C_1$-6", "$C_1$-4" and "$C_2$-6" indicate that the carbon numbers in the groups to which these expressions are attached are respectively within the range of given numbers.

"$C_{1-6}$ alkyl" may be linear or branched, examples of which include methyl, ethyl, n-propyl, isopropyl, n-butyl, isobutyl, sec-butyl, tert-butyl, n-pentyl and n-hexyl. Of these, methyl, ethyl, n-propyl, isopropyl and n-butyl are preferred. Also "$C_{2-6}$ alkyl" encompasses those groups defined as to above $C_{1-6}$ alkyl except methyl, among which ethyl, n-propyl, isopropyl and n-butyl are preferred.

"$C_{2-6}$ alkenyl" can have one or plural double bonds at optional position(s) and may be linear or branched, of which specific examples include vinyl, allyl, isopropenyl, 1-butenyl, 2-butenyl, 3-butenyl, 1,3-butadienyl, 2-methylallyl, 1-pentenyl and 1-hexenyl, among which vinyl, allyl and isopropenyl are preferred.

"$C_{1-6}$ alkoxy" is oxy (0) group substituted with $C_{1-6}$ alkyl, of which specific examples include methoxy, ethoxy, n-propoxy, isopropoxy, n-butoxy, isobutoxy, sec-butoxy, tert-butoxy, n-pentyloxy and n-hexyloxy. Of those, methoxy, ethoxy, n-propoxy, isopropoxy and n-butoxy are preferred.

"$C_{1-6}$ alkylthio" is thio (S) group substituted with $C_{1-6}$ alkyl, of which specific examples include methylthio, ethylthio, n-propylthio, isopropylthio, n-butylthio, isobutylthio, sec-butylthio, tert-butylthio, n-pentylthio and n-hexylthio. Of those, methylthio, ethylthio, n-propylthio, isopropylthio and n-butylthio are preferred.

"$C_{1-4}$ alkylenedioxy" includes, for example, methylenedioxy, ethylenedioxy, propylenedioxy and tetramethylenedioxy. Of those, methylenedioxy and ethylenedioxy are preferred.

"4-7-Membered cycloalkyl" includes cyclobutyl, cyclopentyl, cyclohexyl and cycloheptyl. Of those, cyclopentyl and cyclohexyl are preferred.

"Halogen atom" includes fluorine, chlorine, bromine and iodine, with fluorine, chlorine and bromine being particularly preferred.

"$C_{1-6}$ haloalkyl containing 1-6 halogen atoms" signifies $C_{1-6}$ alkyl following the earlier given definition, which are substituted with same or different 1-6 halogen atoms, of which specific examples include fluoromethyl, trifluoromethyl, 1,2-dichloroethyl, 1-chloro-2-bromoethyl, pentafluoroethyl, 1-chloro-n-propyl, 2-bromo-2-methylethyl, 3-chloro-n-pentyl and 2-bromo-3-chloro-n-hexyl. Of those, $C_{1-2}$ alkyl substituted with same or different 1-5 halogen atoms are preferred.

Also "$C_{1-6}$ haloalkyloxy containing 1-6 halogen atoms" signifies oxy (0) group substituted with above "$C_{1-6}$ haloalkyl containing 1-6 halogen atoms", and "$C_{1-6}$ haloalkylthio containing 1-6 halogen atoms" signifies thio (S) group substituted with above "$C_{1-6}$ haloalkyl containing 1-6 halogen atoms".

"$C_{1-6}$ alkoxy$C_{1-6}$ alkyl" in the definition of $R^1$ in the formula (I) signifies $C_{1-6}$ alkyl substituted with $C_{1-6}$ alkoxy following the earlier given definition, of which specific examples include methoxymethyl, methoxyethyl, methoxy-n-propyl, methoxy-n-butyl, methoxy-n-hexyl, ethoxymethyl, isopropoxymethyl, ethoxyethyl and n-butoxy-n-propyl. Of those, methoxymethyl, methoxyethyl, ethoxymethyl and ethoxyethyl are preferred.

"Phenyl$C_{1-6}$ alkyl" in the definition of $R^2$ in the Formula (I) signifies $C_{1-6}$ alkyl following its definition as given earlier, which is substituted with phenyl; and "carbamoyl$C_{1-6}$ alkyl", the $C_{1-6}$ alkyl following the earlier given definition, which is substituted with carbamoyl (—$CONH_2$); and "amino$C_{1-6}$ alkyl", the $C_{1-6}$ alkyl following the earlier given definition, which is substituted with amino (—$NH_2$).

"$C_{1-6}$ alkylamino$C_{1-6}$ alkyl" in the definition of $R^3$ in the formula (I) signifies the above amino$C_{1-6}$ alkyl whose amino group is further substituted with one of $C_{1-6}$ alkyl groups following the earlier given definition; and "di-($C_{1-6}$ alkyl)amino$C_{1-6}$ alkyl" signifies the same as above except that the amino group is substituted with two of the $C_{1-6}$ alkyl groups following the earlier given definition. The two $C_{1-6}$ alkyl substituting an amino group in di-($C_{1-6}$ alkyl)amino$C_{1-6}$ alkyl may be the same or different.

"$C_{1-6}$ alkylthio" in the definition of $R^3$ signifies thio (S) group substituted with the $C_{1-6}$ alkyl following the earlier given definition, and "$C_{1-6}$ alkoxycarbonyl" in the definition of Y in the formula (I) signifies carbonyl (CO) substituted with the $C_{1-6}$ alkoxy group following the earlier given definition.

"Aromatic carbocyclic group" in the definition of Y encompasses $C_{6-20}$ aromatic carbocyclic groups, of which specific examples include phenyl, 1-indenyl, 1-naphthyl, 2-naphthyl, 2-anthryl and 1-acenaphthenyl. Of those, phenyl and 1-naphthyl are preferred.

"Aromatic heterocyclic group" in the definition of Y encompasses monocyclic or polycyclic aromatic heterocyclic compounds containing 1 or 2 hetero atoms selected from N, O and S, of which one ring is 5- or 6-membered. Specific examples include pyrrolyl, furyl, thienyl, imidazolyl, pyrazolyl, oxazolyl, isoxazolyl, thiazolyl, pyridyl, pyrazinyl, pyrimidinyl, pyridazinyl, indolyl, benzimidazolyl, benzoxazolyl, benzthiazolyl, quinolyl, isoquinolyl and quinazolyl. Of those, monocyclic aromatic heterocyclic groups are preferred.

As "4-7-membered cycloalkenyl" in the definition of Y, for example, 1-cyclobutenyl, 1-cyclopentenyl, 1-cyclohexenyl, 1-cycloheptenyl, 2-cyclobutenyl, 2-cyclopentenyl and 3-cyclohexenyl can be named. Of those, 1-cyclohexenyl and 2-cyclohexenyl are preferred.

As "5-7-membered saturated heterocyclic group containing 1 or 2 nitrogen atoms" in the definition of Y, for example, pyrrolidinyl, piperidinyl, piperazinyl and azepinyl can be named. Of those, piperidinyl and piperazinyl are preferred.

As "5-7-membered saturated heterocyclic group forming a condensed ring with 5- or 6-membered saturated cyclic group and containing 1 or 2 nitrogen atoms" in the definition of Y, for example, hexahydrocyclopenta[b]pyrrolyl, hexahydrocyclopenta[c]pyrrolyl, octahydrocyclopenta[b]pyridyl, octahydrocyclopenta[b]pyridyl, decahydrocyclopenta[b]azepinyl, octahydroindolyl, octahydroisoindolyl, decahydroquinolyl, decahydroisoquinolyl, dodecahydrobenzo[b]azepinyl, octahydropyrrolo[2,3-d]pyridyl, octahydropyrrolo[1,2-a]pyrazyl, octahydropyrido[1,2-a]pyrimidinyl, decahydrophthalazinyl, decahydronaphthyridinyl and decahydroquinazolinyl.

Specifically preferred compounds for use in the methods and kits of the invention include the following and pharmaceutically acceptable salts of such compounds as set forth in the below Table B. As referred to herein, "a compound of Table B" refers to any of the compounds depicted in the immediately below Table B:

TABLE B

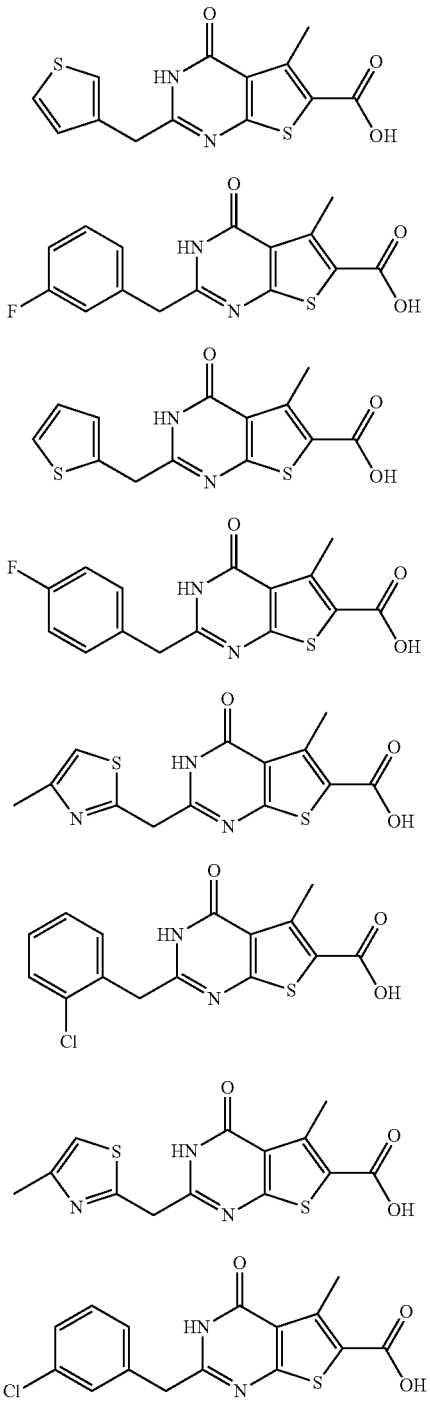

TABLE B-continued
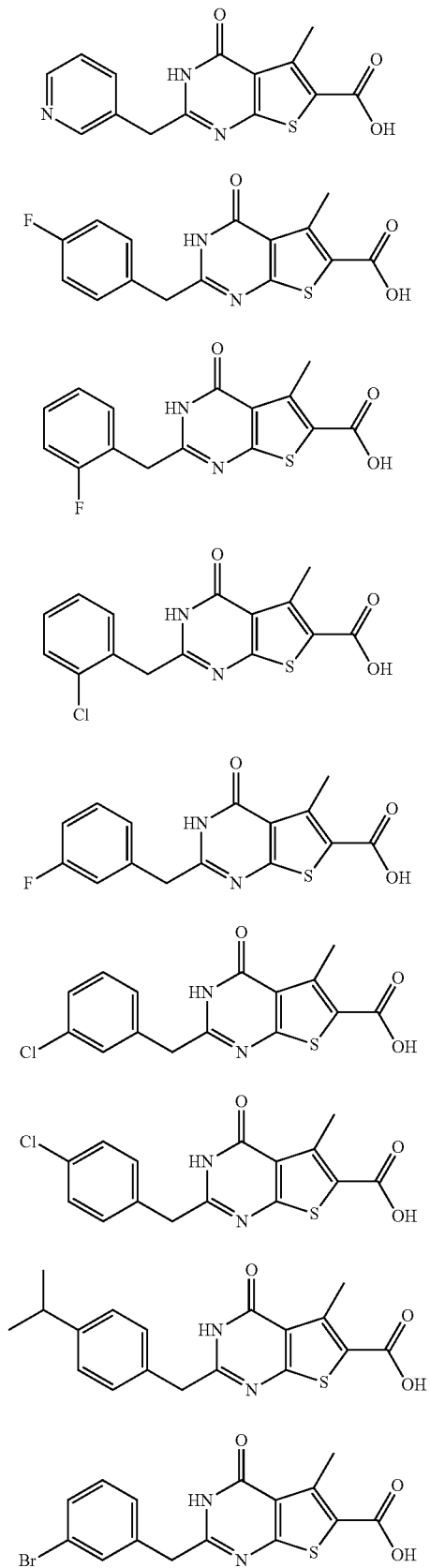
TABLE B-continued
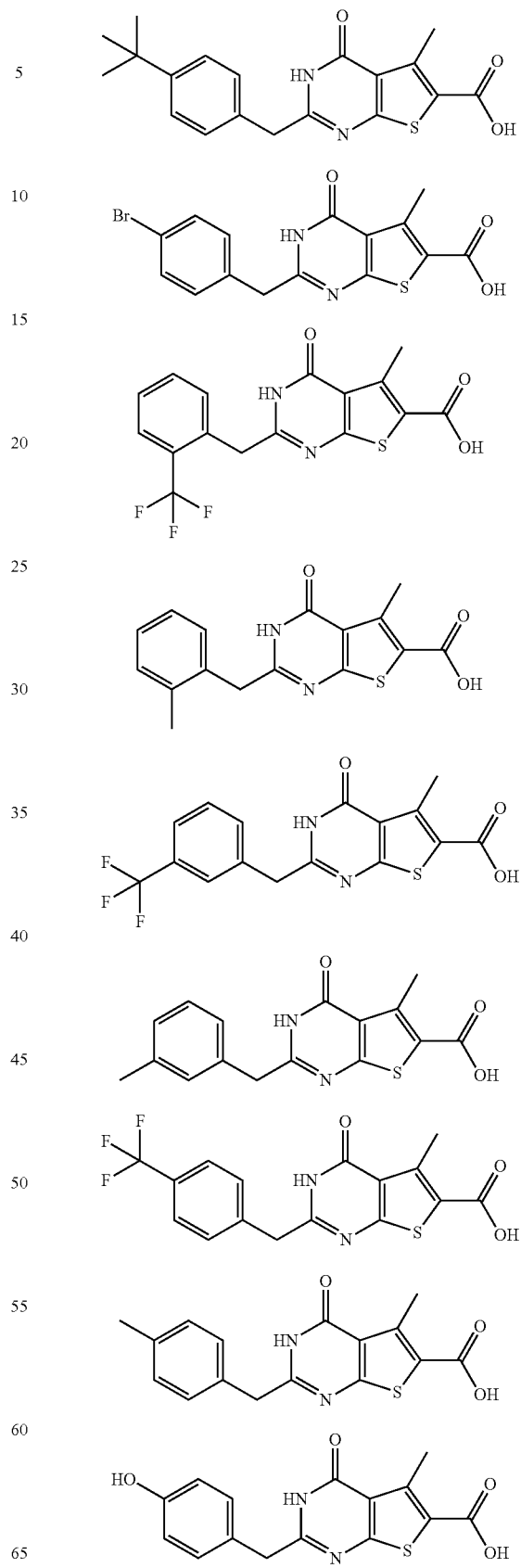

TABLE B-continued
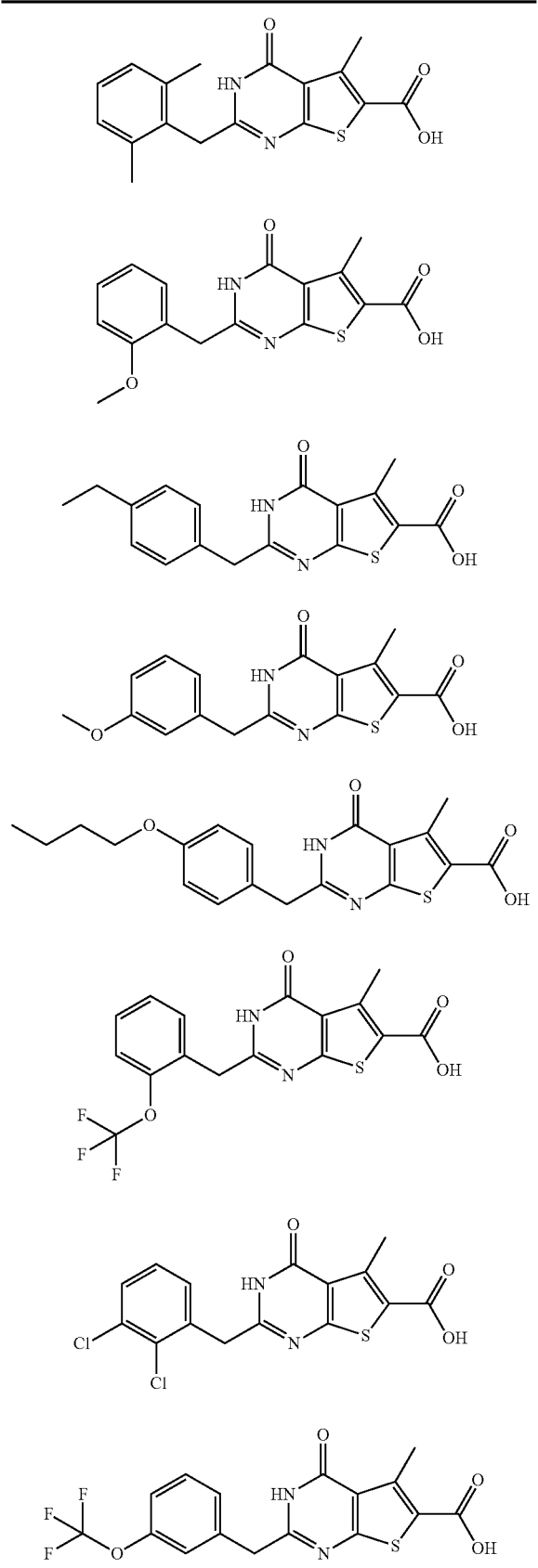
TABLE B-continued
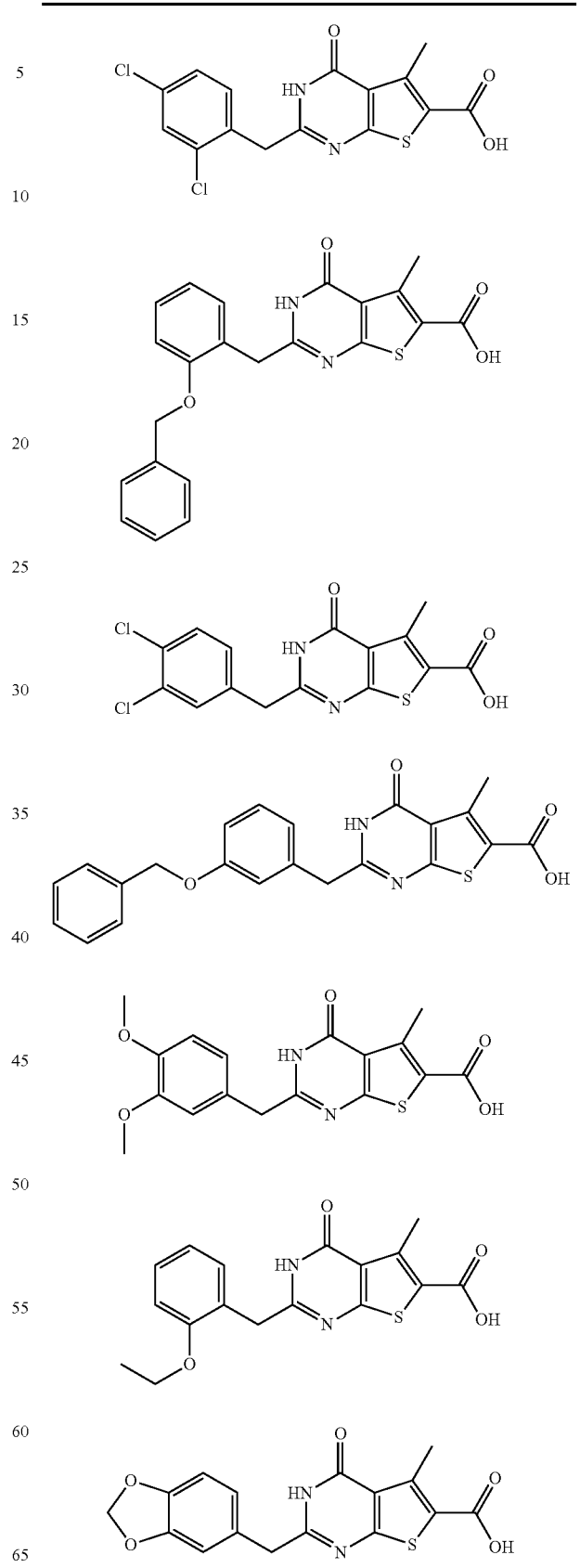

TABLE B-continued
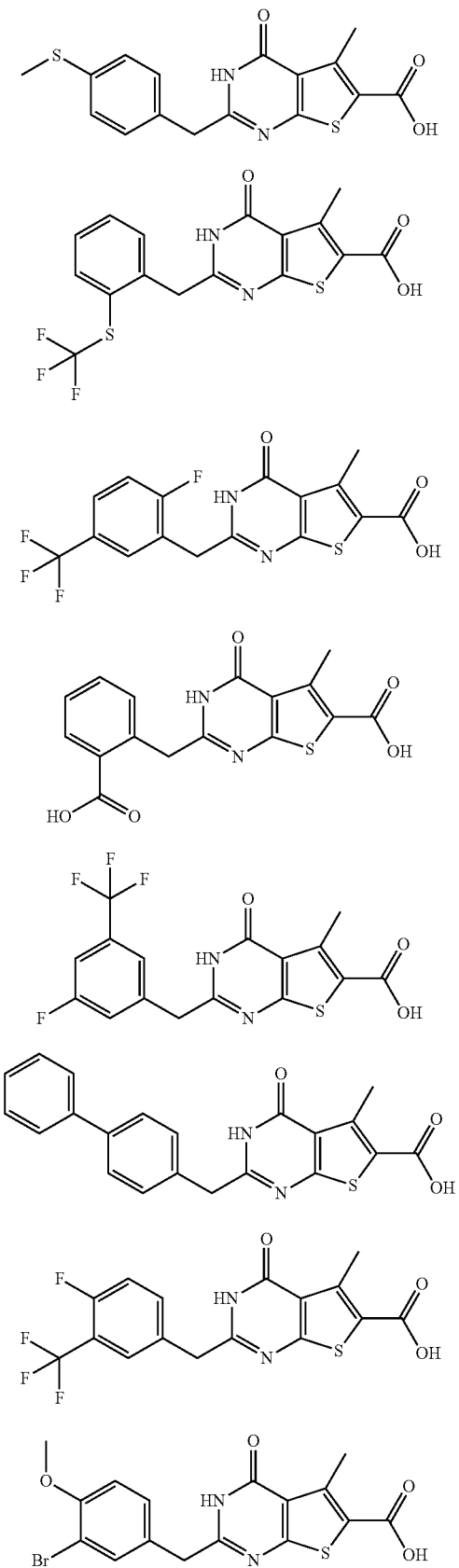
TABLE B-continued
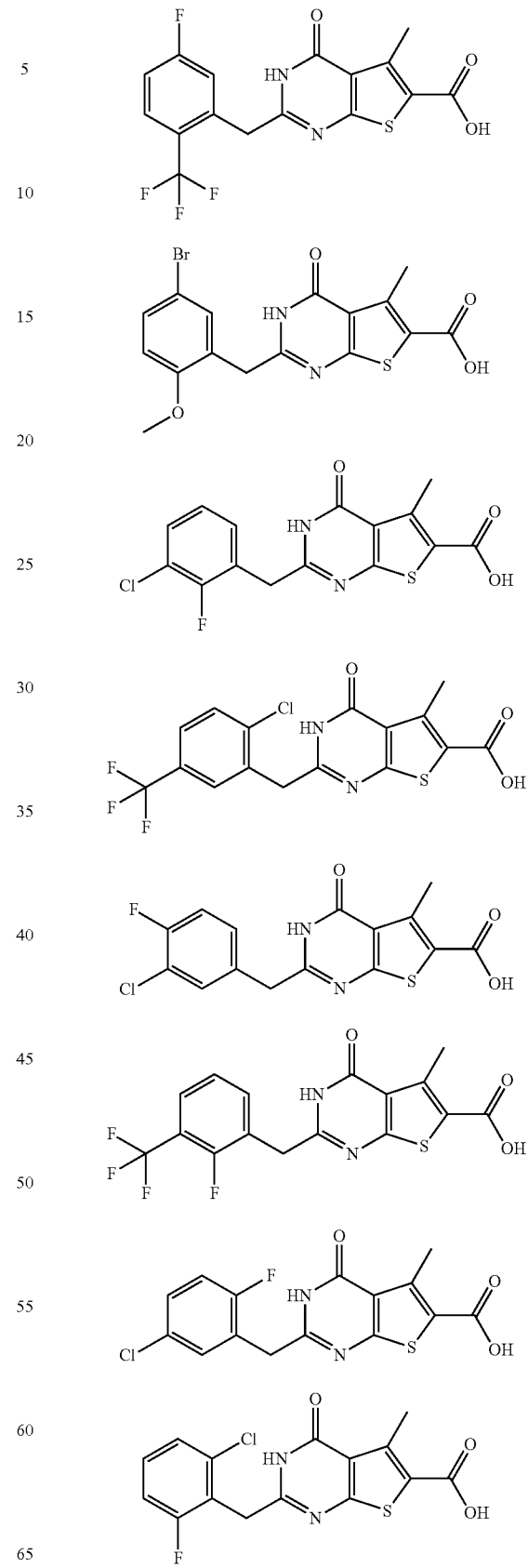

TABLE B-continued
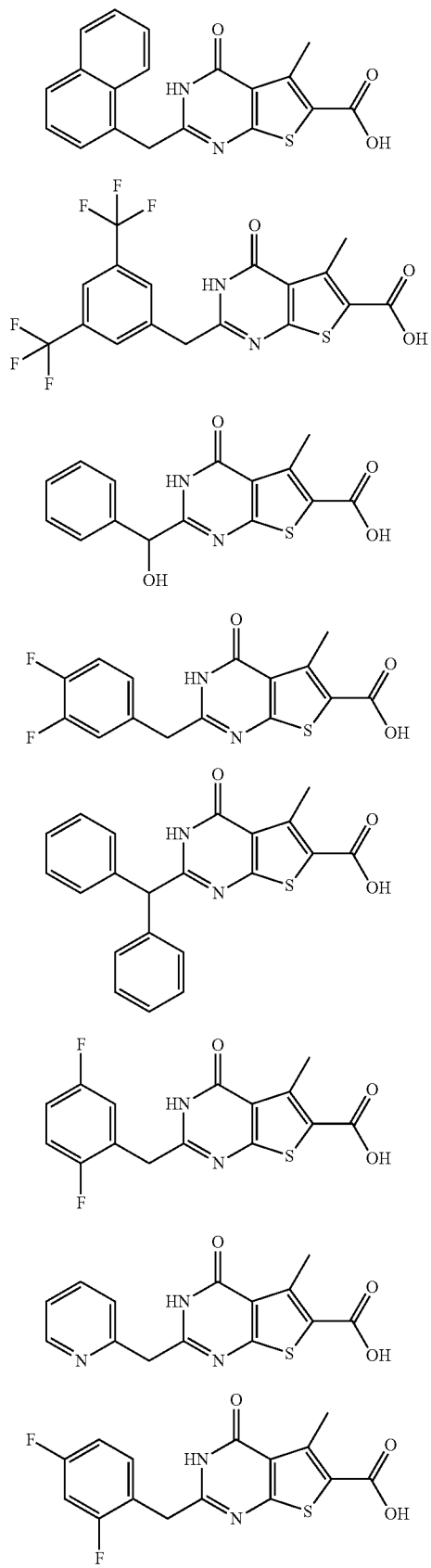
TABLE B-continued
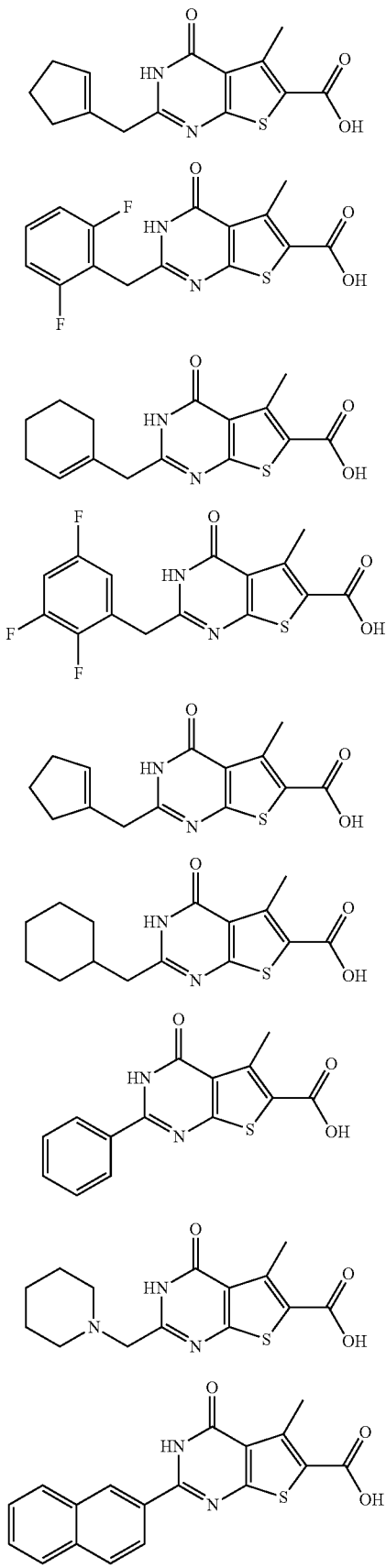

TABLE B-continued
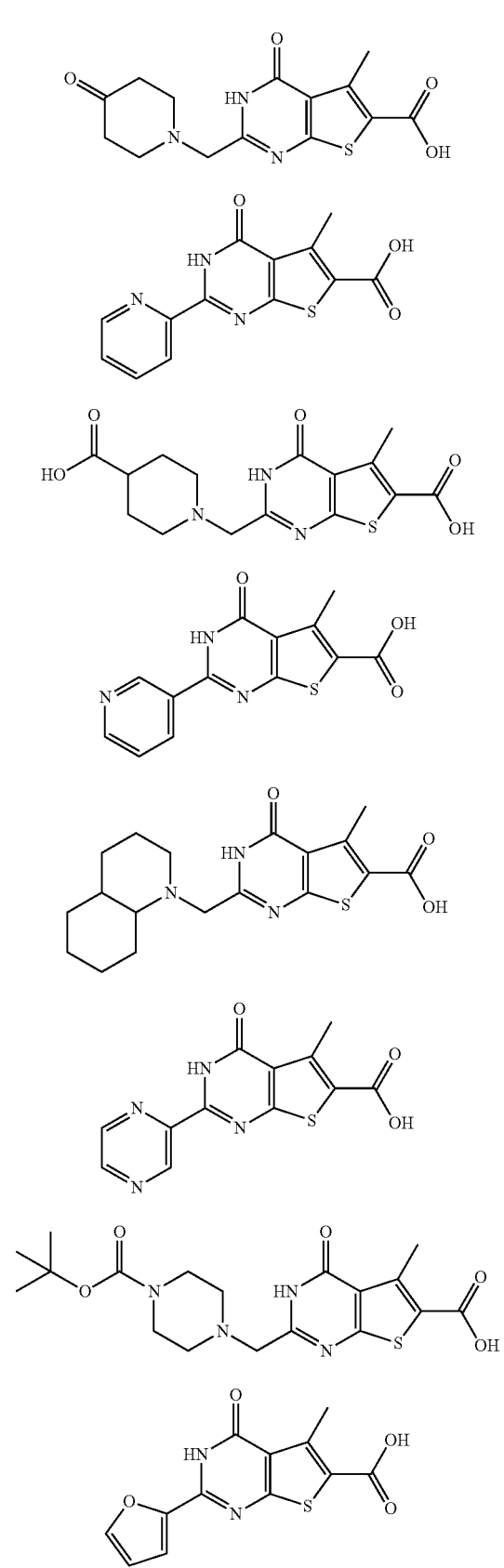
TABLE B-continued
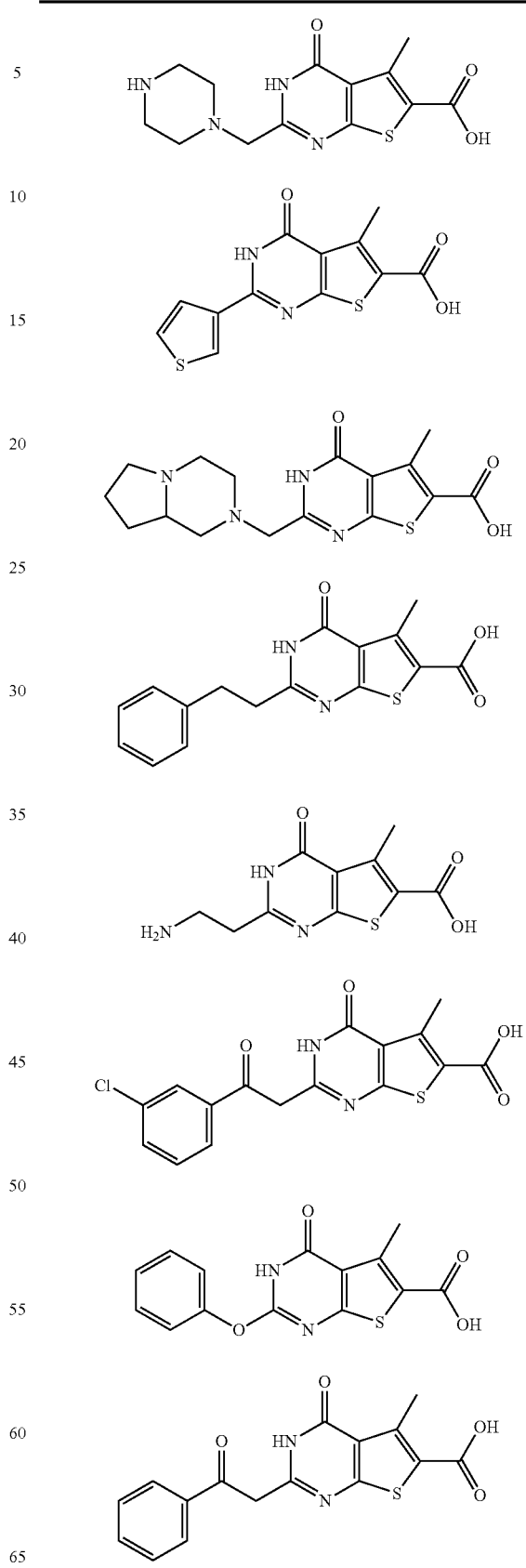

TABLE B-continued
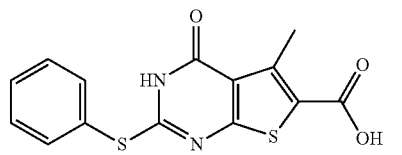 [SMILES: Cc1c(C(=O)O)sc2nc(Sc3ccccc3)[nH]c(=O)c12]
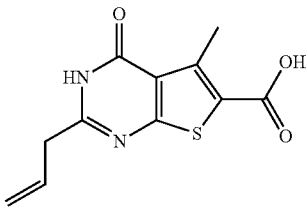 [SMILES: C=CCc1nc2sc(C(=O)O)c(C)c2c(=O)[nH]1]
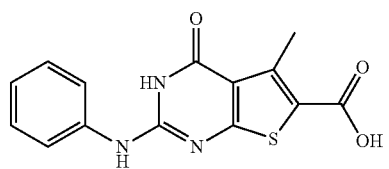 [SMILES: Cc1c(C(=O)O)sc2nc(Nc3ccccc3)[nH]c(=O)c12]
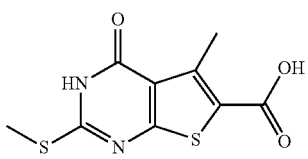 [SMILES: CSc1nc2sc(C(=O)O)c(C)c2c(=O)[nH]1]
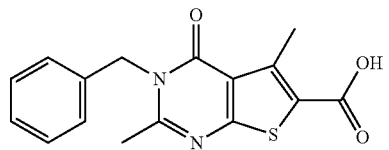 [SMILES: Cc1c(C(=O)O)sc2nc(C)n(Cc3ccccc3)c(=O)c12]
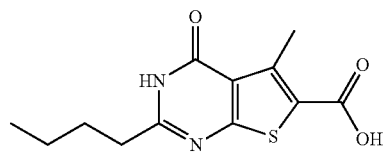 [SMILES: CCCCc1nc2sc(C(=O)O)c(C)c2c(=O)[nH]1]
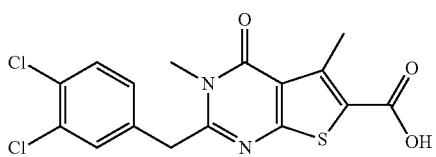 [SMILES: Cc1c(C(=O)O)sc2nc(Cc3ccc(Cl)c(Cl)c3)n(C)c(=O)c12]
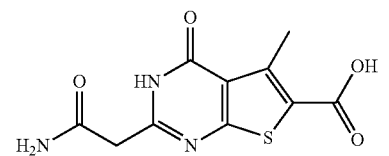 [SMILES: Cc1c(C(=O)O)sc2nc(CC(N)=O)[nH]c(=O)c12]
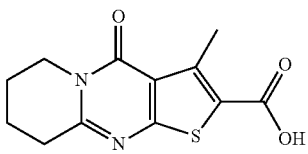 [SMILES: Cc1c(C(=O)O)sc2nc3n(c(=O)c12)CCCC3]
TABLE B-continued
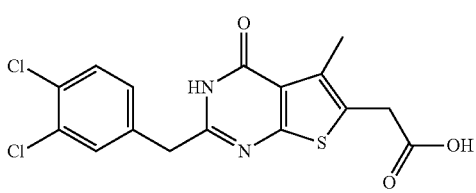 [SMILES: Cc1c(CC(=O)O)sc2nc(Cc3ccc(Cl)c(Cl)c3)[nH]c(=O)c12]
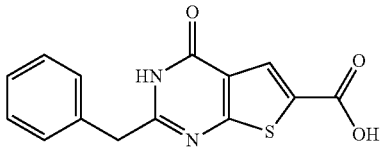 [SMILES: O=C(O)c1cc2c(=O)[nH]c(Cc3ccccc3)nc2s1]
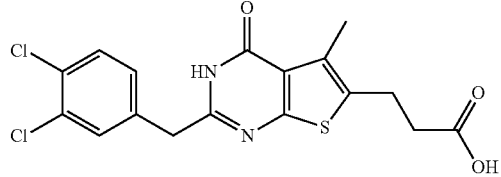 [SMILES: Cc1c(CCC(=O)O)sc2nc(Cc3ccc(Cl)c(Cl)c3)[nH]c(=O)c12]
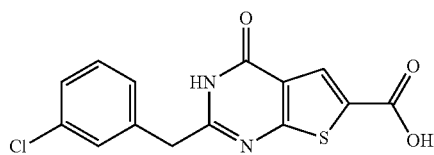 [SMILES: O=C(O)c1cc2c(=O)[nH]c(Cc3cccc(Cl)c3)nc2s1]
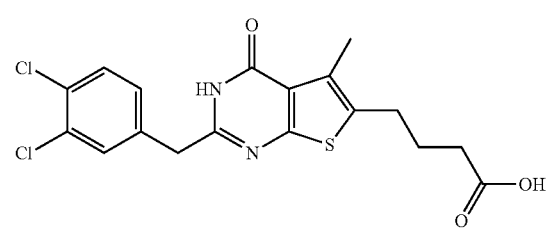 [SMILES: Cc1c(CCCC(=O)O)sc2nc(Cc3ccc(Cl)c(Cl)c3)[nH]c(=O)c12]
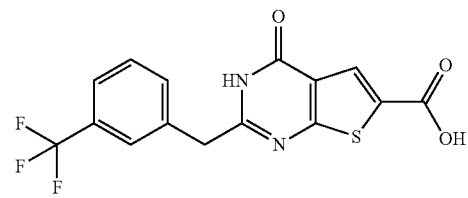 [SMILES: O=C(O)c1cc2c(=O)[nH]c(Cc3cccc(C(F)(F)F)c3)nc2s1]
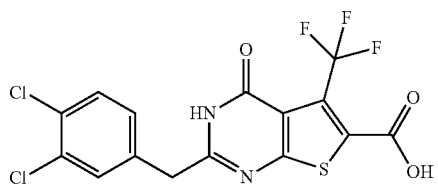 [SMILES: O=C(O)c1sc2nc(Cc3ccc(Cl)c(Cl)c3)[nH]c(=O)c2c1C(F)(F)F]
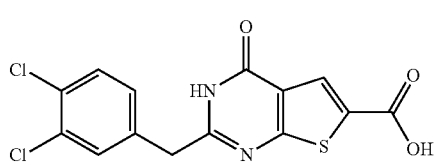 [SMILES: O=C(O)c1cc2c(=O)[nH]c(Cc3ccc(Cl)c(Cl)c3)nc2s1]

TABLE B-continued

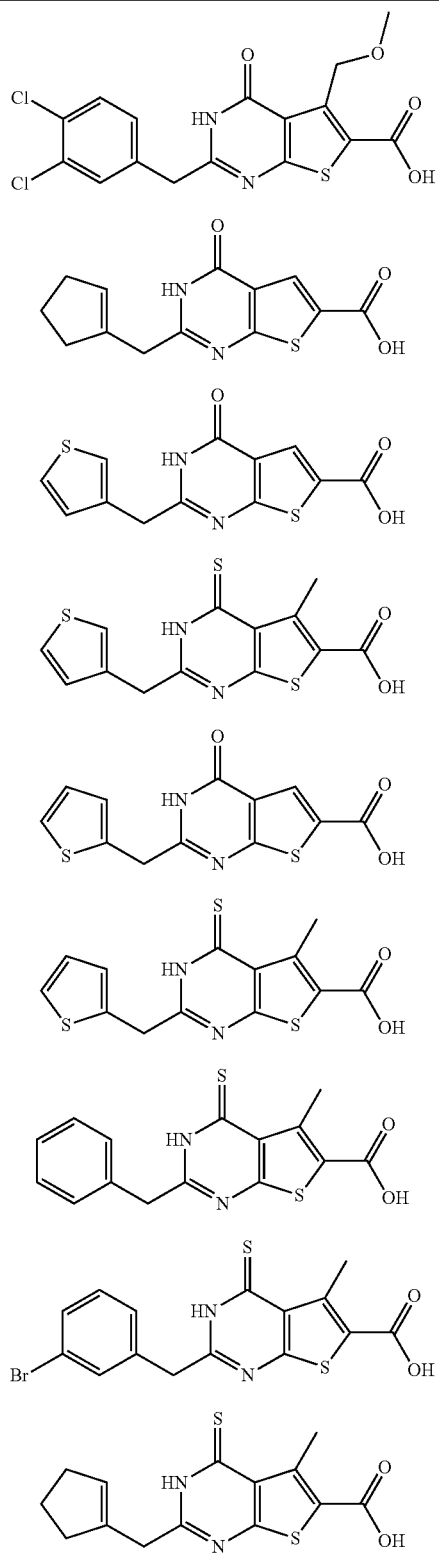

TABLE B-continued

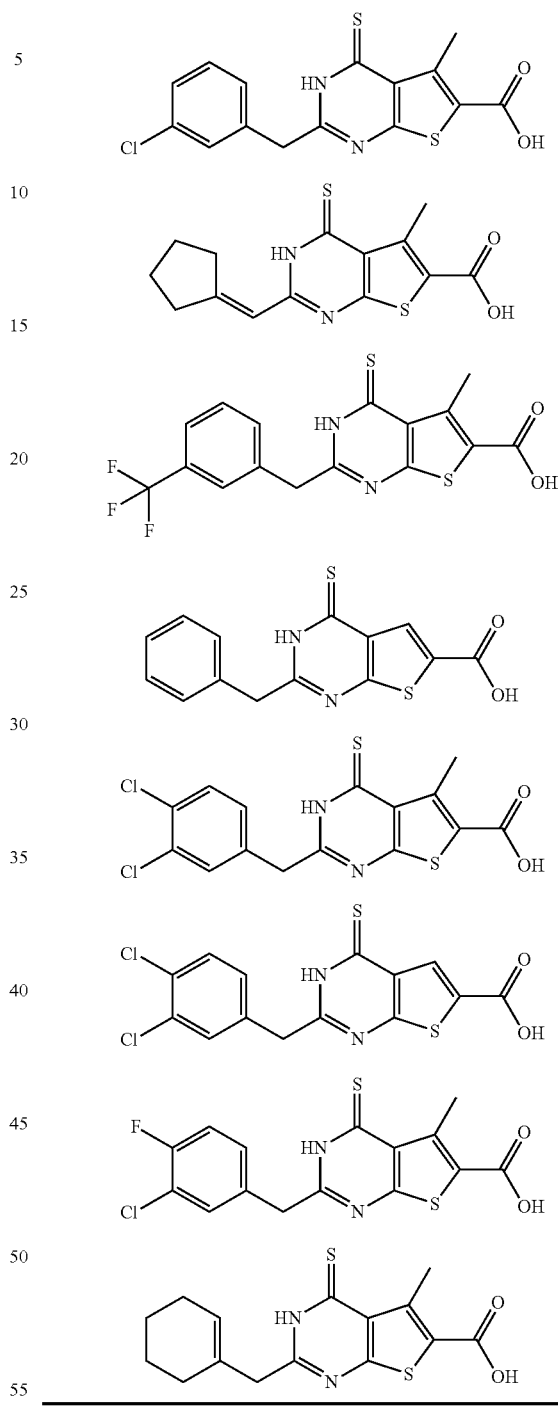

Additional preferred compounds for use in the present methods and kits include the following and pharmaceutically acceptable salts of such compounds. The following compounds and pharmaceutically acceptable salts thereof are referred to herein as compounds of Table C:

TABLE C 2-benzyl-4-oxo-3,4-dihydrothieno[2,3-d]pyrimidine-6-carboxylic acid,
2-(5-chlorothiophen-2-ylmethyl)-4-oxo-3,4-dihydrothieno-[2,3-d]pyrimidine-6-carboxylic acid,
2-(2-fluorobenzyl)-4-oxo-3,4-dihydrothieno[2,3-d]pyrimidine-6-carboxylic acid, TABLE C-continued 2-(3-fluorobenzyl)-4-oxo-3,4-dihydrothieno[2,3-d]pyrimidine-6-carboxylic acid,
2-(4-fluorobenzyl)-4-oxo-3,4-dihydrothieno[2,3-d]pyrimidine-6-carboxylic acid,
2-(2-chlorobenzyl)-4-oxo-3,4-dihydrothieno[2,3-d]pyrimidine-6-carboxylic acid,
2-(4-chlorobenzyl)-4-oxo-3,4-dihydrothieno[2,3-d]pyrimidine-6-carboxylic acid,
2-(3-bromobenzyl)-4-oxo-3,4-dihydrothieno[2,3-d]pyrimidine-6-carboxylic acid,
2-(3-methylbenzyl)-4-oxo-3,4-dihydrothieno[2,3-d]pyrimidine-6-carboxylic acid,
4-oxo-2-(2-trifluoromethylbenzyl)-3,4-dihydrothieno-[2,3-d]pyrimidine-6-carboxylic acid,
2-(cyclohexen-1-ylmethyl)-4-oxo-3,4-dihydrothieno[2,3-d]-pyrimidine-6-carboxylic acid,
5-methyl-4-oxo-2-(thiophen-2-yl)-3,4-dihydrothieno-[2,3-d]pyrimidine-6-carboxylic acid,
2-(α-hydroxythiophen-2-ylmethyl)-5-methyl-4-oxo-3,4-dihydrothieno[2,3-d]pyrimidine-6-carboxylic acid,
5-methyl-4-oxo-2-[(2-thiophen-2-yl)ethyl]-3,4-dihydrothieno-[2,3-d]pyrimidine-6-carboxylic acid,
5-methyl-4-oxo-2-(thiophen-2-ylcarbonyl)-3,4-dihydrothieno-[2,3-d]pyrimidine-6-carboxylic acid,
5-methyl-4-oxo-2-(thiophen-2-ylsulfanyl)-3,4-dihydrothieno-[2,3-d]pyrimidine-6-carboxylic acid,
5-methyl-4-oxo-2-(thiophen-2-yloxy)-3,4-dihydrothieno[2,3-d]-pyrimidine-6-carboxylic acid,
5-methyl-4-oxo-2-(thiophen-2-ylamino)-3,4-dihydrothieno-[2,3-d]pyrimidine-6-carboxylic acid,
2-(5-fluorothiophen-2-ylmethyl)-5-methyl-4-oxo-3,4-dihydrothieno[2,3-d]pyrimidine-6-carboxylic acid,
2-(5-bromothiophen-2-ylmethyl)-5-methyl-4-oxo-3,4-dihydrothieno[2,3-d]pyrimidine-6-carboxylic acid,
5-methyl-2-(5-methylthiophen-2-ylmethyl)-4-oxo-3,4-dihydrothieno[2,3-d]pyrimidine-6-carboxylic acid,
2-(5-fluorothiophen-3-ylmethyl)-5-methyl-4-oxo-3,4-dihydrothieno[2,3-d]pyrimidine-6-carboxylic acid,
2-(5-chlorothiophen-3-ylmethyl)-5-methyl-4-oxo-3,4-dihydrothieno[2,3-d]pyrimidine-6-carboxylic acid,
2-(5-bromothiophen-3-ylmethyl)-5-methyl-4-oxo-3,4-dihydrothieno[2,3-d]pyrimidine-6-carboxylic acid,
5-methyl-2-(5-methylthiophen-3-ylmethyl)-4-oxo-3,4-dihydrothieno[2,3-d]pyrimidine-6-carboxylic acid,
2-(furan-2-ylmethyl)-5-methyl-4-oxo-3,4-dihydrothieno-[2,3-d]pyrimidine-6-carboxylic acid,
2-(furan-3-ylmethyl)-5-methyl-4-oxo-3,4-dihydrothieno-[2,3-d]pyrimidine-6-carboxylic acid,
2-(5-chlorofuran-2-ylmethyl)-5-methyl-4-oxo-3,4-dihydrothieno[2,3-d]pyrimidine-6-carboxylic acid,
2-(5-chlorofuran-3-ylmethyl)-5-methyl-4-oxo-3,4-dihydrothieno[2,3-d]pyrimidine-6-carboxylic acid,
2-(5-chlorooxazol-2-ylmethyl)-5-methyl-4-oxo-3,4-dihydrothieno[2,3-d]pyrimidine-6-carboxylic acid,
5-methyl-4-oxo-2-(pyridin-4-ylmethyl)-3,4-dihydrothieno[2,3-d]pyrimidine-6-carboxylic acid,
5-methyl-4-oxo-2-(pyrimidin-2-ylmethyl)-3,4-dihydrothieno[2,3-d]pyrimidine-6-carboxylic acid,
2-(4-methoxybenzyl)-5-methyl-4-oxo-3,4-dihydrothieno-[2,3-d]pyrimidine-6-carboxylic acid,
2-(3,5-dichlorobenzyl)-5-methyl-4-oxo-3,4-dihydrothieno-[2,3-d]pyrimidine-6-carboxylic acid,
2-(4-chloro-3-fluorobenzyl)-5-methyl-4-oxo-3,4-dihydrothieno-[2,3-d]pyrimidine-6-carboxylic acid,
2-(4-chloro-3-methylbenzyl)-5-methyl-4-oxo-3,4-dihydrothieno-[2,3-d]pyrimidine-6-carboxylic acid,
2-(4-chloro-3-trifluoromethylbenzyl)-5-methyl-4-oxo-3,4-dihydrothieno[2,3-d]pyrimidine-6-carboxylic acid,
2-(3-chloro-5-trifluoromethylbenzyl)-5-methyl-4-oxo-3,4-dihydrothieno[2,3-d]pyrimidine-6-carboxylic acid,
2-(3-carboxybenzyl)-5-methyl-4-oxo-3,4-dihydrothieno-[2,3-d]pyrimidine-6-carboxylic acid,
2-(3-ethoxycarbonylbenzyl)-5-methyl-4-oxo-3,4-dihydrothieno-[2,3-d]pyrimidine-6-carboxylic acid,
2-(3-aminobenzyl)-5-methyl-4-oxo-3,4-dihydrothieno[2,3-d]-pyrimidine-6-carboxylic acid,
5-methyl-2-(3-nitrobenzyl)-4-oxo-3,4-dihydrothieno-[2,3-d]pyrimidine-6-carboxylic acid,
3-amino-2-benzyl-5-methyl-4-oxo-3,4-dihydrothieno-[2,3-d]pyrimidine-6-carboxylic acid,
3-amino-5-methyl-4-oxo-2-(thiophen-2-ylmethyl)-3,4-dihydrothieno-[2,3-d]pyrimidine-6-carboxylic acid,
3-amino-5-methyl-4-oxo-2-(thiophen-3-ylmethyl)-3,4-dihydrothieno[2,3-d]pyrimidine-6-carboxylic acid,
3-amino-2-(5-chlorothiophen-2-ylmethyl)-5-methyl-4-oxo-3,4-dihydrothieno[2,3-d]pyrimidine-6-carboxylic acid,
3-amino-2-(2-fluorobenzyl)-5-methyl-4-oxo-3,4-dihydrothieno-[2,3-d]pyrimidine-6-carboxylic acid,
3-amino-2-(3-fluorobenzyl)-5-methyl-4-oxo-3,4-dihydrothieno-[2,3-d]pyrimidine-6-carboxylic acid,
3-amino-2-(4-fluorobenzyl)-5-methyl-4-oxo-3,4-dihydrothieno-[2,3-d]pyrimidine-6-carboxylic acid,
3-amino-2-(2-chlorobenzyl)-5-methyl-4-oxo-3,4-dihydrothieno-[2,3-d]pyrimidine-6-carboxylic acid,
3-amino-2-(3-chlorobenzyl)-5-methyl-4-oxo-3,4-dihydrothieno-[2,3-d]pyrimidine-6-carboxylic acid,
3-amino-2-(4-chlorobenzyl)-5-methyl-4-oxo-3,4-dihydrothieno-[2,3-d]pyrimidine-6-carboxylic acid,
3-amino-2-(3,4-dichlorobenzyl)-5-methyl-4-oxo-3,4-dihydrothieno[2,3-d]pyrimidine-6-carboxylic acid,
3-amino-2-(3-bromobenzyl)-5-methyl-4-oxo-3,4-dihydrothieno-[2,3-d]pyrimidine-6-carboxylic acid,
3-amino-5-methyl-2-(3-methylbenzyl)-4-oxo-3,4-dihydrothieno-[2,3-d]pyrimidine-6-carboxylic acid,
3-amino-5-methyl-4-oxo-2-(2-trifluoromethylbenzyl)-3,4-dihydrothieno[2,3-d]pyrimidine-6-carboxylic acid,
3-amino-5-methyl-4-oxo-2-(3-trifluoromethylbenzyl)-3,4-dihydrothieno[2,3-d]pyrimidine-6-carboxylic acid,
3-amino-2-(cyclopenten-1-ylmethyl)-5-methyl-4-oxo-3,4-dihydrothieno[2,3-d]pyrimidine-6-carboxylic acid, and
3-amino-2-(cyclohexen-1-ylmethyl)-5-methyl-4-oxo-3,4-dihydrothieno[2,3-d]pyrimidine-6-carboxylic acid.

Thienopyrimidine compounds for use in the present methods and kits can be synthesized by known procedures, including those procedures disclosed in U.S. Pat. No. 8,293,754 to Gotanda et al. Thienopyrimidines can be synthesized by annulation of the pyrimidine nucleus on the parent thiophene ring or annulation of a thiophene nucleus on the parent pyrimidine ring. See Abdel-Megid et al., *J. Pharm. Appl Chem.*, 2, No. 3, 103-127 (2016).

The subject to be administered with one or more thienopyrimidine compounds as disclosed herein is suitably a mammal, or particularly a human. In some embodiments, the method of treating heart failure may further comprise a step of selecting the subject suffering from or susceptible to heart failure, including a subject that has suffered from or is susceptible to congestive heart failure of acute cardiogenic shock.

In additional embodiments, the method of treating heart failure may further comprise a step of selecting the subject suffering from or susceptible to cardiac hypertrophy, heart failure with preserved ejection fraction (HfpEF), heart failure with reduced ejection fraction (HFrEF) (reduced systolic function), reduced diastolic function, maladaptive hypertrophy, heart failure with preserved systolic function, diastolic heart failure, hypertensive heart disease, aortic stenosis, hypertrophic cardiomyopathy, and/or post ischemic cardiac remodeling.

In some embodiments, one or more thienopyrimidine compounds as disclosed herein may be administered in combination with one or more additional distinct heart failure therapeutic agents. Exemplary agents for co-administration include Angiotensin-Converting Enzyme (ACE) Inhibitors such as Captopril (Capoten), Enalapril (Vasotec), Fosinopril (Monopril), Lisinopril (Prinivil, Zestril), Perindopril (Aceon), Quinapril (Accupril), Ramipril (Altace) and Trandolapril (Mavik); Angiotensin II Receptor Blockers (or Inhibitors) such as Candesartan (Atacand), Losartan (Cozaar), and Valsartan (Diovan); Neprilysin inhibitors alone or in combinations, such as Angiotensin-Receptor Neprilysin Inhibitors (ARNIs) combinations like sacubitril/valsartan (Entresto), I$_f$-Channel Blocker (or inhibitor) such as Ivabradine (Corlanor); Beta Blockers such as Bisoprolol (Zebeta), Metoprolol succinate (Toprol XL), Carvedilol (Coreg), and Carvedilol CR (Coreg CR)Toprol XL; Aldosterone Antagonists such as Spironolactone (Aldactone), and Eplerenone (Inspra); Hydralazine and isosorbide dinitrate; Diuretics such as Furosemide (Lasix), Bumetanide (Bumex), Torsemide (Demadex), Chlorothiazide (Diuril), Amiloride (Midamor Chlorthalidone (Hygroton), Hydro-chlorothiazide (Esidrix, Hydrodiuril), Indapamide (Lozol), Metolazone (Zaroxolyn) and Triamterene (Dyrenium); Anticoagulants (blood thinners); and/or Cholesterol lowering drugs (statins).

Therapeutically effective dosages of a thienopyrimidine compound as disclosed herein may vary rather widely and may be adjusted or selected to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Suitable effective dosages may range from 0.01 to 5 or 10 mg/kg per day, although dosages outside such ranges also may be utilized as appropriate.

The therapeutically effective dose of the compound can be administered to the subject by a variety of administration routes. Oral or topical administration will be typically preferred although other administration protocols also may be utilized as parenteral, sublingual, or via an implanted reservoir. In some embodiments, the compound may be formulated for administering purposes in a capsule, a tablet, a gel, a powder, liquid, suspension or emulsion.

As discussed, therapeutic compositions are also provided that include one or more compounds as disclosed herein optionally with a pharmaceutically acceptable carrier.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

In one preferred aspect, the compound may be formulated for administering purposes in a capsule, a tablet, a gel, a powder, liquid, suspension or emulsion; however, the administering methods may not be particularly limited.

In some embodiments, the therapeutically effective dose of the compound may be administered orally, parenterally, buccal, sublingually, or via an implanted reservoir The compound(s) can be included in a kit, container, pack, or dispenser together with instructions for administration. For instance, the kit may contain a product label or written package insert that discloses use of the composition for treating including prophylaxis of heart failure.

The following non-limiting examples are illustrative of the invention.

Example 1

This Example can show whether the PDE9 Inhibitor (PDE9i) has any beneficial effect in preclinical models of the cardiovascular syndrome of heart failure using a standard mouse cardiovascular model of heart failure. The approach includes testing the effects of PDE9i on pre-established myocardial hypertrophy in the mouse transverse aortic constriction (TAC) model. The hypothesis being tested is that PDE9i will prevent and/or inhibit the development and extent of heart failure and hemodynamic dysfunction in this model of heart failure.

The study is performed to: 1) to test the safety of oral gavage administration of 2000 mg/kg/day of study drug, or maximum dose able to be diluted in 220-250 μL of solvent (equaling a volume not exceeding 10 mL/kg/dose); and 2) to bank and store heart, other systemic tissue, and blood to enable measurement of cGMP if desired.

Mice are randomized to study drug or vehicle at Day 0. Mice each receives drug ideally once every 24 hours, or alternatively every 12 hours, with a goal of administering 2000 mg/kg/day. Mice are monitored twice daily for signs of distress and weighed daily to ensure normal food intake. Mice also are monitored for body condition score. At Day 7 mice are anesthetized with inhaled isoflurane (3.5%). Blood (1 mL) and hearts are removed and stored at −80°. Other target organs including kidneys, liver, lungs, and spleen are removed and frozen as well. A small portion of organs are separated and stored in 10% formalin to enable future histologic examination of tissues if desired.

Study groups (mice experimental groups) are treated as follows:
1) Vehicle (10 mL/kg); n=6
2) ASP4901 (2000 mg/kg in volume of 10 mL/kg); n=6

Example 2

Pressure overload is performed by surgical placement of suture around the transverse aorta (Transverse aortic constriction, TAC). For these PDE9i studies, size-, age- and sex-matched (male) C57BL/6J mice are randomized to receive vehicle alone or PDE9i (initially at dose of 2000 mg/kg).

For these chronic drug treatment studies, animals are randomized to receive vehicle or PDE9i daily by oral gavage at Day −7 to establish steady-state levels of PDE9i.

On day 0, mice undergo 1 of 2 procedures: sham surgery or TAC, resulting in these 4 experimental groups as shown in Table 1.

TABLE 1

| Group | Surgery | Drug/dose | N |
|---|---|---|---|
| 1 | Sham | Vehicle (10 mL/kg/day) | 10 |
| 2 | Sham | ASP4901 (2000 mg/kg/day) | 10 |
| 3 | TAC | Vehicle (10 mL/kg/day) | 20 |
| 4 | TAC | ASP4901 (2000 mg/kg/day) | 20 |

A total of 10 male C57/BL6 mice 8 to 10 weeks of age (22-25 g weight) are used in each sham group. A total of 20 male C57/BL6 mice 8 to 10 weeks of age (22-25 g weight) are used in each TAC group, in order to achieve an expected 10-15 TAC mice surviving to day 28. In this long-term study, the surviving animals in each group (as explained above), undergo echocardiography on: the day of drug randomization (days −7), the day of surgery (day 0), and on the day of terminal harvest (day 28), followed by invasive hemodynamic evaluation and sacrifice at the end of the study.

Following the terminal hemodynamic studies, mice are euthanized for tissue analysis. Tissue histology studies are performed following the terminal hemodynamic studies. Plasma aliquots are saved and frozen for determination of the free plasma concentration of PDE9i and potential biomarkers if an efficacy signal is obtained.

For all of these studies, in vivo analysis and post-mortem myocardial analysis are performed with investigators blinded as to experimental group. In TAC mice, analysis is restricted to mice demonstrating an expected increase in left ventricle (LV) pressure (>20 mmHg mercury TAC gradient as assessed at time of harvest).

Endpoints:

Effects of chronic PDE9i treatment alone on mortality and cardiac function following pressure overload-induced heart failure are assessed with a standard panel of cardiac hemodynamic function and systemic pressures in all animals. Measurements in the PDE9i-treated, sham-operated group are used to explore whether PDE9i has any independent (drug-induced) effects on cardiovascular function in the absence of any pressure overload from TAC.

Animals TAC are performed as described in reference 1 below and references within. All procedures are performed under general anesthesia using 2.0% to 2.5% isoflurane. For the sham and TAC operations, mice are anesthetized, intubated, and ventilated with a small animal respirator (Harvard Rodent Ventilator, Model 683, Natick, Mass.). A left thoracotomy are performed. TAC are induced by tying a 7-0 polypropylene suture around the transverse aorta, against a 27-gauge needle.

Echocardiography.

Transthoracic echocardiography is performed under light sedation with 1.5% isoflurane administered via nose cone while the core body temperature is maintained at 37.0° C. Analysis of the echocardiographic images is performed by a blinded investigator. LV end-diastolic diameter (EDD) and LV end-systolic diameter (ESD) is measured directly, and LV fractional shortening (FS) is determined using the standard equation FS=(EDD-ESD)/EDD. Chamber dimensions are also be indexed to tibia length (TL) that can be measured postmortem to the nearest 0.01 mm with a microcaliper (Fisher Scientific).

Terminal Hemodynamic Evaluation.

Terminal hemodynamic evaluation is performed using 2.0% isoflurane anesthesia administered via nose cone. Pressures are acquired sequentially from the left internal carotid, right internal carotid, and the left ventricle. Pressure-volume loop analysis is performed.

Tissue Harvest At sacrifice, the heart is arrested in diastole by the intravenous injection of 0.3 mL of 1M KCl; the heart is then rapidly removed and the right ventricular free wall carefully separated from the LV. All tissues are weighed. LV weights are indexed to TL to the nearest 0.01 mm with a microcaliper. At sacrifice, a small portion (10 to 20 mg) of the LV base is removed and snap-frozen in liquid nitrogen and stored at −70° C. for future protein and RNA extraction, as needed. The middle portion of the LV, cut in the short axis at the level of the mid-papillary, is fixed in 10% formalin overnight and embedded in paraffin for IHC analyses. The apex of the LV is saved for cGMP concentration measurements.

Histology.

Myocardium is fixed with 10% formaldehyde, paraffin embedded and sectioned into 4-mm slices. Masson's trichrome staining is used to visualize collagen. Quantification of fibrosis content is performed in four to six regions of each heart. Myocyte cross sectional area is measured using an automated algorithm with NIH Image J 1.47i software. Image acquisition will be performed on a Zeiss LSM510-META laser-scanning microscope.

Molecular analyses.

PDE9 expression and cGMP levels are determined, as described in Blanton et al. and references within. cGMP concentrations are determined using a commercially available ELISA kit (GE Healthcare) as described in Takimoto et al and references within.

Data Analyses and Statistics.

The primary endpoint is LV hypertrophy as assayed by LV mass normalized to tibia length. This is compared between experimental groups. Co-secondary endpoints are: a) percent fractional shortening and b) survival, both compared between groups. Secondary analyses are performed on hemodynamic data and indices of LV function. Further secondary analyses include comparison of within-group changes of echocardiographic parameters from day −7 to day 28 (such as relative change in FS % day −7 to day 28), and from day 02 day 28. All data are reported as mean±SEM. Comparisons between groups are performed using the unpaired Student t test. For TAC experiments, comparisons are made by 2-way analysis of variance and P values will be calculated to determine the effect of genotype on the TAC-stimulated response. Correction for multiple comparisons are made using the Student-Newman-Keuls method unless noted. A P value <0.05 is considered statistically significant.

Laboratory Facilities for Studies:

the studies are conducted in a state-of-the-art Mouse Physiology Core facility equipped with three independent and fully functional murine 'operating rooms', each with Zeiss dual operator surgical microscopes with 35 mm Camera adaptor and VHS video/audio taping capabilities with color monitor, Nikon single operator stereomicroscopes, Harvard rodent respirators, table top gas anesthesia machine (VetEquip Inc., Pleasanton Calif.) for rodent inhalation (Isofluorane) anesthesia, Honeywell simultrace physiological recorders with MacLab data acquisition analysis ECG monitoring, Visitech mouse tailcuff blood pressure analysis systems with laptop computer, Harvard syringe infusion pump with microliter per hour capabilities, Microsurgical instruments and supplies/shaver, scale, heated operating surface, heat lamp, oxygen, rectal temperature monitoring, Olympus Bmax U-SPT microscope with Hitachi color video camera, VK-C370 with Sony Trinitron color video monitor PVM 1343MD, coupled with a Power Macintosh computer 7100/66AV with NIH image analysis software.

In addition, the facility includes the equipment necessary to perform continuous ambulatory telemetered EKG monitoring, hemodynamic monitoring and invasive electrophysiological testing. Specifically, it is equipped with a full complement of hemodynamic and ECG monitoring and acquisition equipment including MacLab data acquisition and ECG monitoring, Visitech mouse tailcuff blood pressure analysis system with laptop computer, 1.4f Millar pressure-volumetransducer catheters (#SPR-671), and control unit (#TC510), and control box coupled to an EMKA acquisition card and software that allows real-time viewing and analysis of P-V loops and other in vivo hemodynamic measurements. Additionally, the facility is equipped with a full range of electrophysiology tools including 2Fr. C1Ber mouse EP catheters, implantable ECG monitors for continuous ambulatory telemetric ECG analysis (Data Science Inc.) and Dataquest ART data acquisition and analysis systems interfaced with a dedicated Dell PC for data collection. The MCRI Mouse Physiology Core also has a state of the art, Visualsonics Vevo 2100 ultrasound system dedicated only to research applications to perform high throughput, mouse echocardiography studies. The Visualsonics device contains the full analysis software required for image processing and functional analysis of LV images obtained.

Example 3

(1) Organ Mass Measurements

Organs from the mice experimental groups of Example 1 after surgery (Sham or TAC) and/or treatments (vehicle or ASP4901) were obtained and evaluated. The organ masses from LV (FIG. 1A), HW (FIG. 1B), RV (FIG. 1C), atria (FIG. 1D) and lung (FIG. 1D) were normalized to Tibia Length and results are shown in FIGS. 1A-1E. The organ masses from the group that had TAC surgery and treated with ASP have similar trend with the group had sham surgery (control).

(2) Day 14 Echocardiography Measurements

Figure 2A:
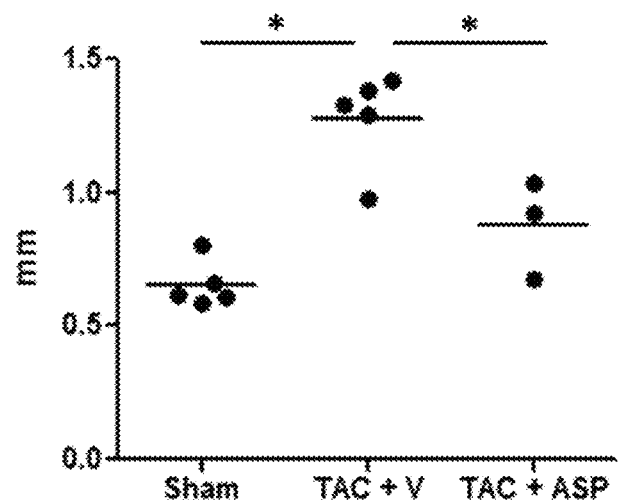
FIG. 2A shows posterior wall thicknesses from the mice experimental groups and FIG. 2B shows anterior wall thicknesses from the mice experimental groups.
Figure 2B:
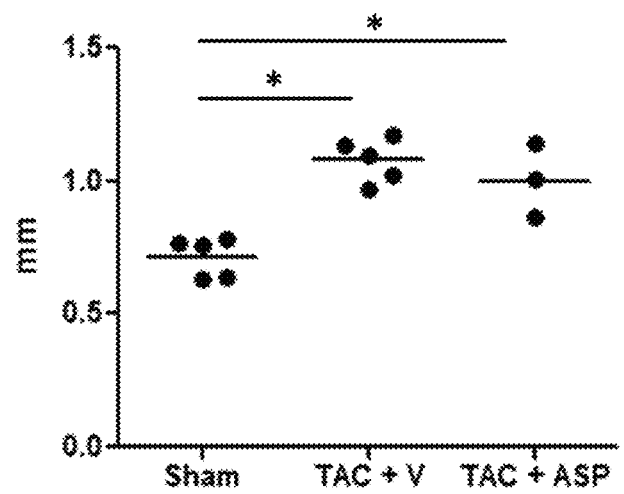

Posterior wall thickness and anterior wall thickness of right ventricle (RV) were measured in each mice experimental group of Example 1 with echocardiography and results are shown in FIGS. 2A-2B. Although slightly different results are shown between anterior and posterior walls, these wall thicknesses were used in the LV mass calculation.

Figure 3A:
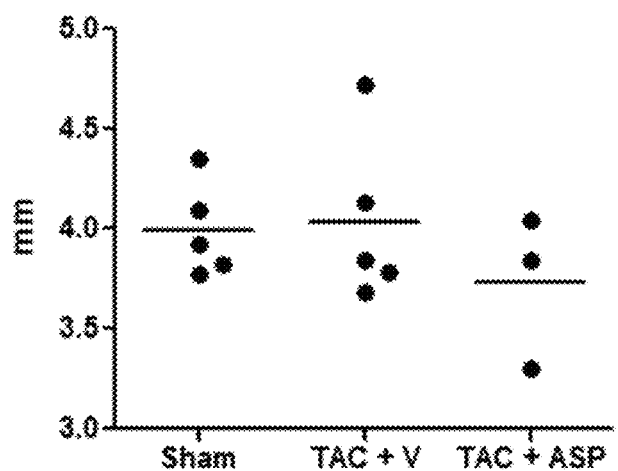
FIG. 3A shows LV end-diastolic diameters (EDD) measured from the mice experimental groups.
Figure 3B:
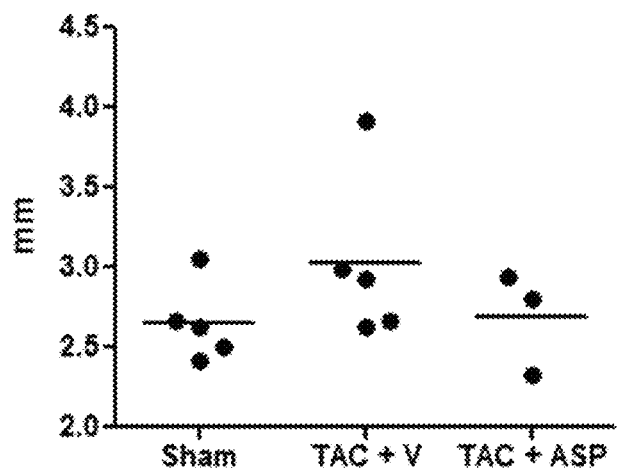
FIG. 3B shows LV end-systolic diameters (ESD) measured from the mice experimental groups.
Figure 3C:
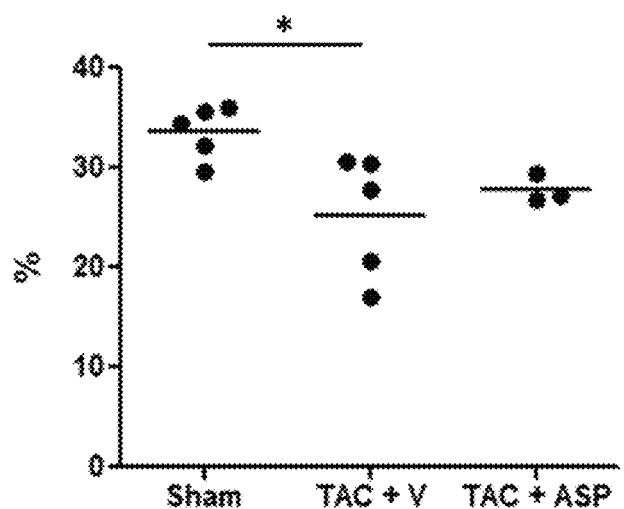
FIG. 3C shows LV fractional shortenings (FS) calculated for the mice experimental groups.
Figure 3D:
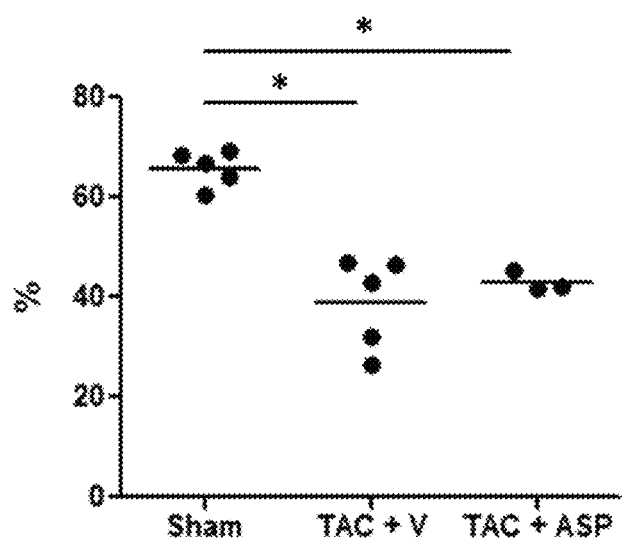
FIG. 3D shows LV ejection fractions measured from the mice experimental groups.

LV end-diastolic diameter (EDD) and LV end-systolic diameter (ESD) were measured in each mice experimental group of Example 1 and the results are shown in FIGS. 3A-3B. Accordingly, LV fractional shortening (FS) was determined as described herein and the results are shown in FIG. 3C. LV ejection fraction was measured from each mice group and results are shown in FIG. 3D. Reduced ejection fractions were observed from the mice experimental group after TAC treated with or without ASP.

Figure 4A:
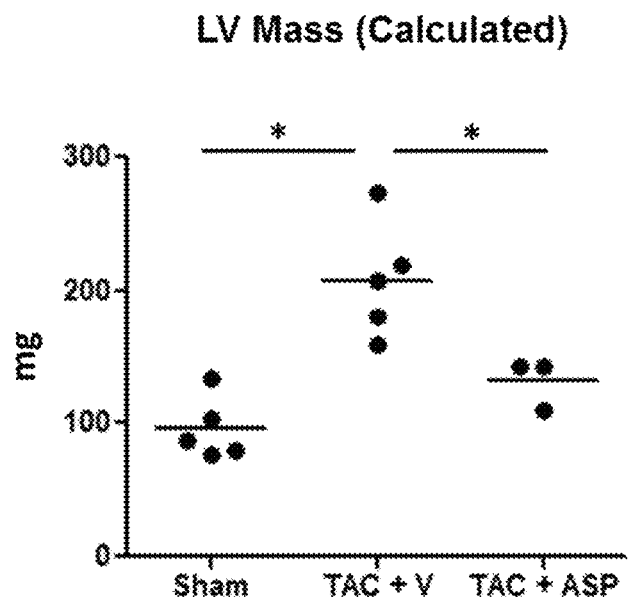
FIG. 4A shows LV masses calculated from echocardiography from the mice experimental groups.
Figure 4B:
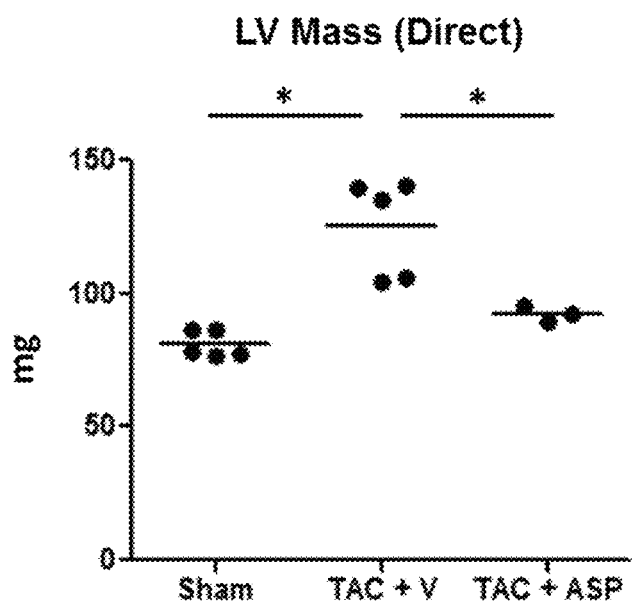
FIG. 4B shows raw LV masses calculated from echocardiography from the mice experimental groups.
Figure 4C:
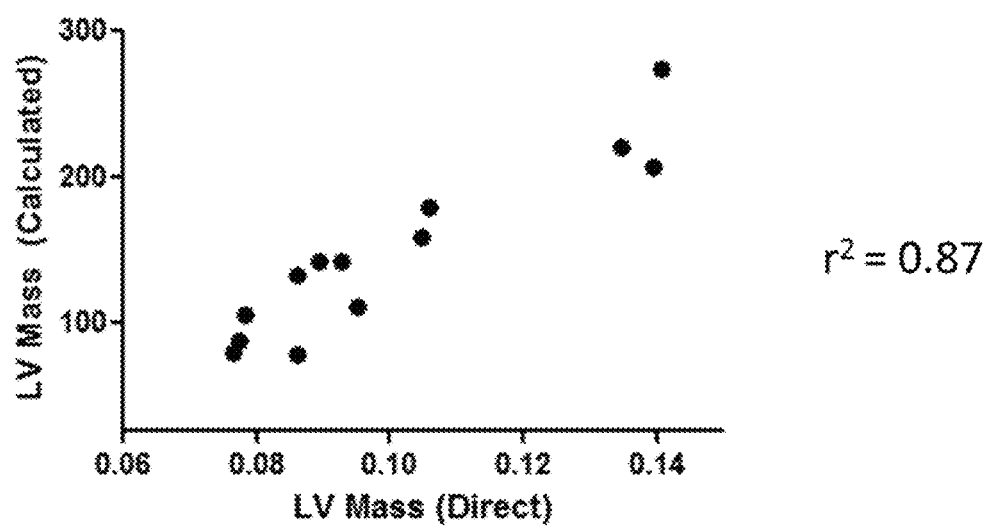
FIG. 4C shows a comparison between the calculated LV masses and the raw LV masses.

In this study, the LV masses can be calculated from echocardiography, which enables us to track LV masses over time. At day 14, raw LV mass (FIG. 4B) from survivors and calculated LV mass (FIG. 4A) were compared in FIG. 4C. The echocardiography-calculated LV mass at day 14 and direct LV mass at harvest correlate well with a high r-squared.

(3) Echocardiography Parameters by Day

Figure 5A:
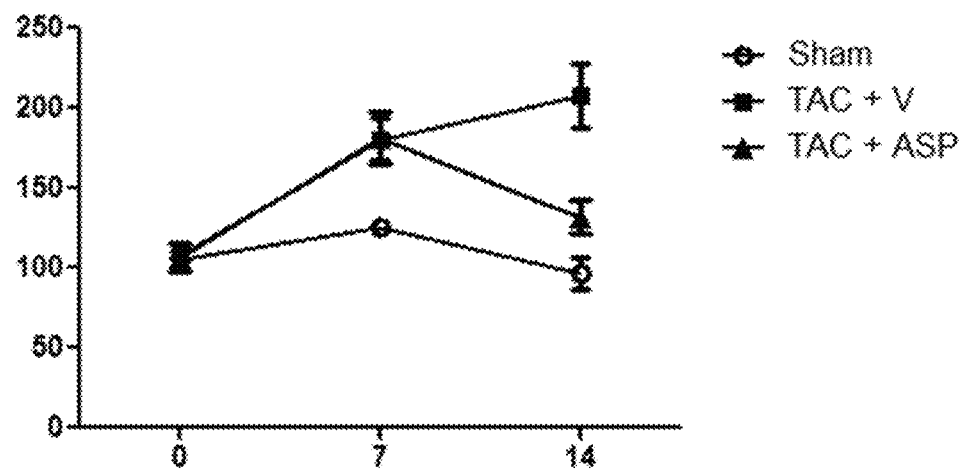
FIG. 5A shows LV masses calculated by echocardiography from the mice experiment groups from day 0 to day 14.
Figure 5B:
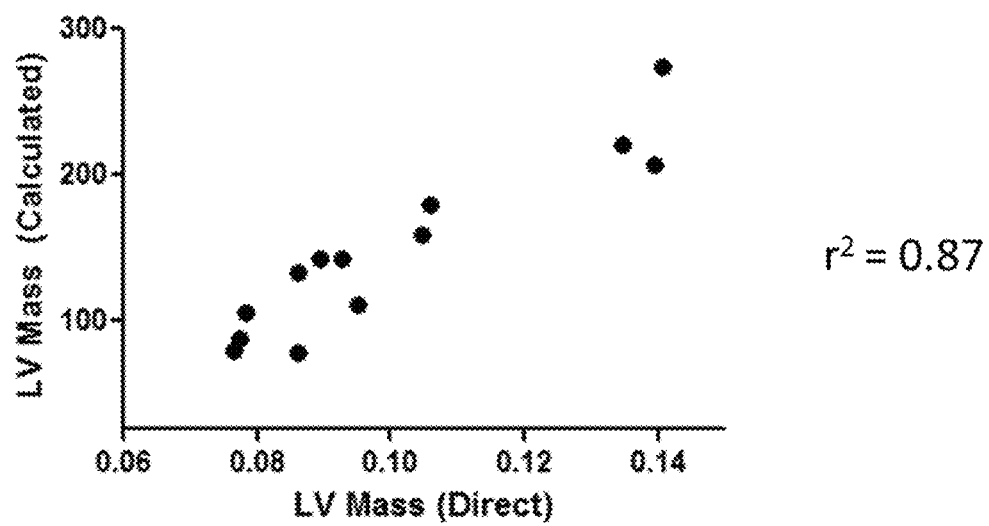
FIG. 5B shows correlation therebetween the calculated and the raw LV masses in the mice experimental groups from day 0 to day 14.
Figure 6A:
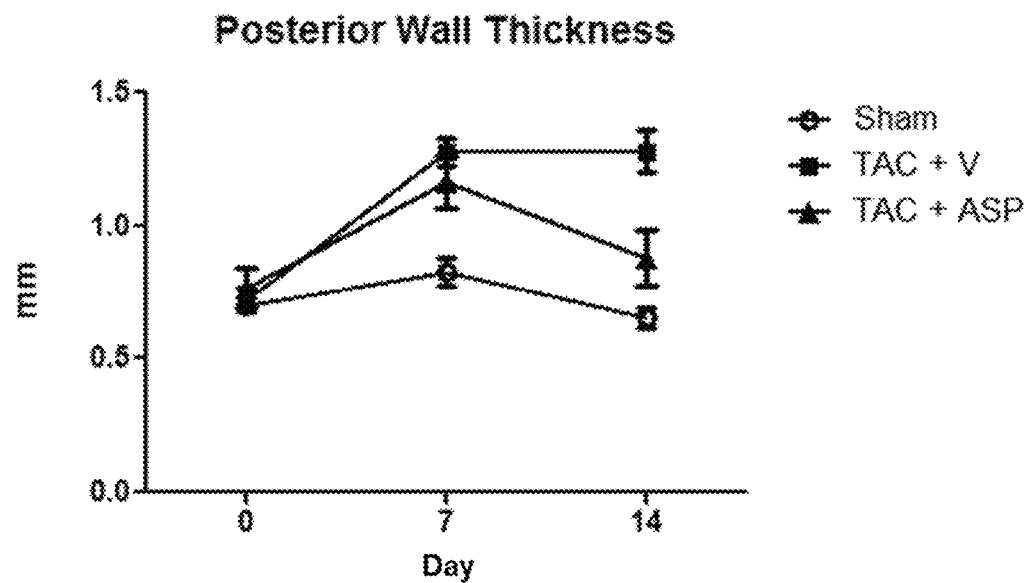
FIG. 6A shows the measured posterior wall thicknesses by echocardiography from the mice experimental groups from day 0 to day 14.
Figure 6B:
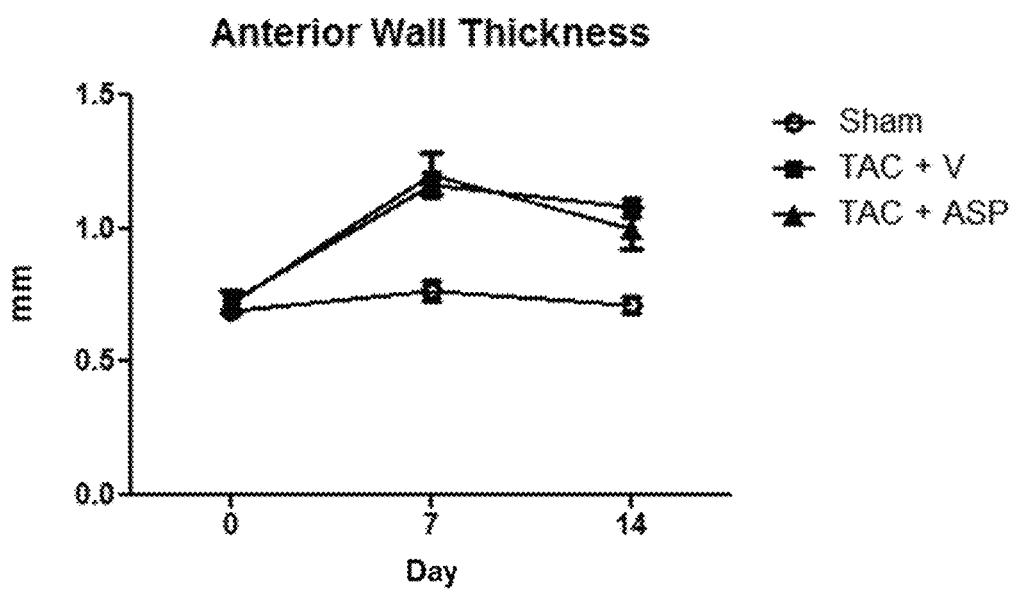
FIG. 6B shows the measured anterior wall thicknesses by echocardiography from the mice experimental groups from day 0 to day 14.
Figure 7A:
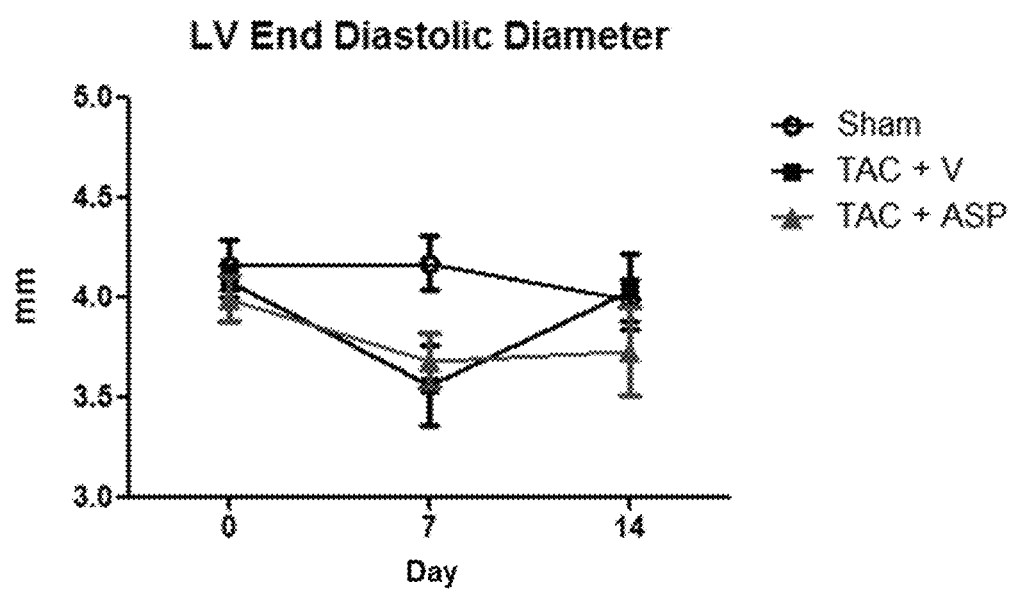
FIG. 7A shows LV end diastolic diameter results from the mice experimental groups from day 0 to day 14.
Figure 7B:
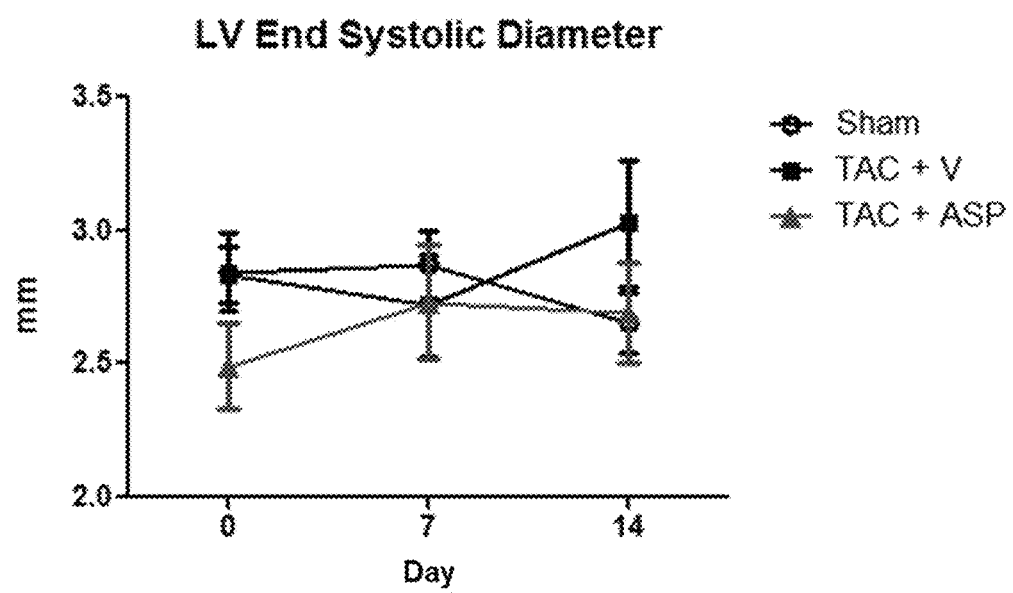
FIG. 7B shows LV end systolic diameter results from the mice experimental groups from day 0 to day 14.
Figure 8A:
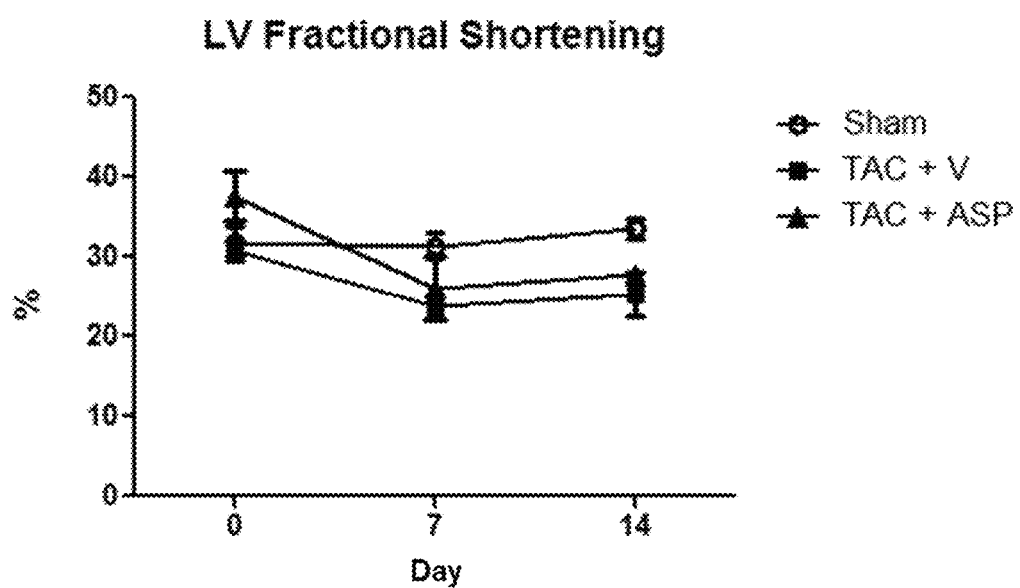
FIG. 8A shows LV fractional shortening results from the mice experimental groups from day 0 to day 14.
Figure 8B:
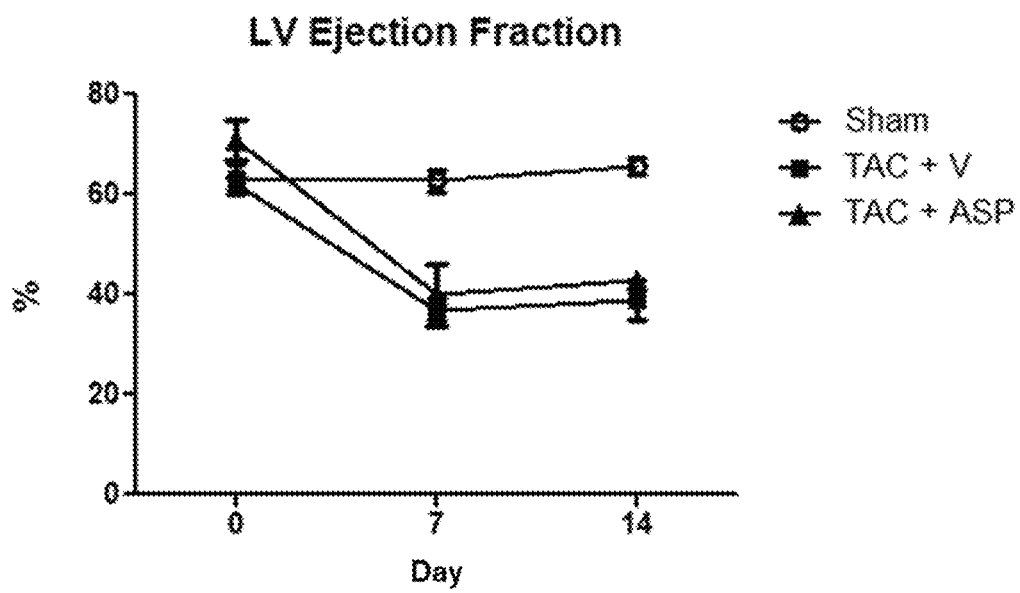
FIG. 8B shows LV ejection fraction results from the mice experimental groups from day 0 to day 14.

The mice experimental groups in Example 1 were evaluated at pre-surgery (day 0), pre-randomization to vehicle or ASP (day 7), and at harvest (day 14, after 7 days of v or ASP administration) by echocardiography parameters. LV masses from each mice experimental group were also calculated by echocardiography in each group from day 0 to day 14 (FIG. 5A). The calculated LV masses were compared with directly measured (raw) masses and shown in regression to confirm correlation therebetween (FIG. 5B). Following measurements of posterior wall thickness and anterior wall thickness were obtained by echocardiography in each group from day 0 to day 14 and the results are shown in FIGS. 6A-6B. In addition, LV end diastolic diameter and LV end systolic diameter in each mice experimental group from day 0 to day 14 are shown in FIG. 7A-7B; and LV fractional shortening and LV ejection fraction from each mice experimental group over 1-14 days are shown in FIG. 8A-8B.

Among others, the mass data (e.g. FIG. 5A) from the mice experimental groups are significant at day 14 by One Way ANOVA with Tukey post-testing. The experimental data provided above can evidence that the drug-treated TAC mice had regression of LV hypertrophy compared with vehicle treated. In addition, reviewing the echocardiography, at the time of randomization, both TAC groups had the same degree of LV hypertrophy and contractile dysfunction, but by day 14, the LVH regressed selectively in the drug-treated group.

REFERENCES

1. Protein kinase Gα inhibits pressure overload-induced cardiac remodeling and is required for the cardioprotective effect of sildenafil in vivo. Blanton R M, Takimoto E, Lane A M, Aronovitz M, Piotrowski R, Karas R H, Kass D A, Mendelsohn M E. J Am Heart Assoc. 2012 Oct.; 1(5):e003731.
2. Chronic inhibition of cyclic GMP phosphodiesterase 5A prevents and reverses cardiac hypertrophy. Takimoto E, Champion HC, Li M, Belardi D, Ren S, Rodriguez E R, Bedja D, Gabrielson K L, Wang Y, Kass D A. Nat Med. 2005 Feb.; 11(2):214-22.

All documents mentioned herein are herein incorporated by reference herein in their entirety.

What is claimed is:

1. A method of treating heart failure in a mammal, the method comprising administering an effective amount of a compound having the structure

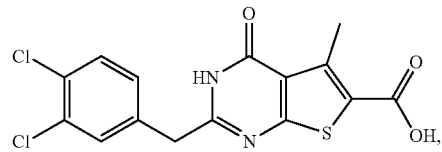 [SMILES: Cc1c(C(=O)O)sc2nc(Cc3ccc(Cl)c(Cl)c3)[nH]c(=O)c12]

or a pharmaceutically acceptable salt thereof.

2. The method of claim 1 wherein the mammal is identified as exhibiting congestive heart failure.

3. The method of claim 2 wherein the mammal has suffered from congestive heart failure disorder having low cardiac output and/or low stroke volume.

4. The method of claim 1 claim wherein the mammal has suffered from cardiogenic shock.

5. The method of claim 1 wherein the mammal is a human.

6. The method of claim 5 wherein the compound is co-administered with one or more Angiotensin-Converting Enzyme (ACE) Inhibitors; Angiotensin II Receptor Blockers or Inhibitors; Angiotensin-Receptor Neprilysin Inhibitors (ARNIs; Beta Blockers; Aldosterone Antagonists; Diuretics; Anticoagulants (blood thinners); and/or Cholesterol lowering drugs.

7. The method of claim 1 wherein the effective amount is from 0.01 to 10 mg/kg per day.

8. The method of claim 1 wherein the compound is comprised in a pharmaceutical composition further comprising a pharmaceutically acceptable carrier.

9. The method of claim 8 wherein the pharmaceutical composition is formulated for administering purposes in a capsule, a tablet, a gel, a powder, liquid, suspension or emulsion.

\* \* \* \* \*